(12) United States Patent
Gielen et al.

(10) Patent No.: US 8,600,495 B2
(45) Date of Patent: *Dec. 3, 2013

(54) TECHNIQUES FOR POSITIONING THERAPY DELIVERY ELEMENTS WITHIN A SPINAL CORD OR BRAIN

(75) Inventors: Frans Gielen, Eckelrade (NL); Gary W. King, Fridley, MN (US); Daryle Petersen, Eagan, MN (US); Mark T. Rise, Monticello, MN (US); Michael Schendel, Andover, MN (US); Warren Starkebaum, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/794,363

(22) Filed: Jun. 4, 2010

(65) Prior Publication Data
US 2010/0241179 A1 Sep. 23, 2010

Related U.S. Application Data

(60) Continuation of application No. 11/669,758, filed on Jan. 31, 2007, now Pat. No. 7,734,342, which is a continuation of application No. 10/881,239, filed on Jun. 30, 2004, now Pat. No. 7,191,018, which is a continuation of application No. 09/934,001, filed on Aug. 21, 2001, now Pat. No. 6,795,737, which is a division of application No. 09/303,145, filed on Apr. 30, 1999, now Pat. No. 6,319,241, which is a continuation-in-part of application No. 09/070,136, filed on Apr. 30, 1998, now Pat. No. 6,161,047.

(51) Int. Cl.
*A61N 1/00* (2006.01)

(52) U.S. Cl.
USPC .............................................................. 607/3

(58) Field of Classification Search
None
See application file for complete search history.

(56) References Cited

U.S. PATENT DOCUMENTS

| | | |
|---|---|---|
| 4,141,365 A | 2/1979 | Fischell |
| 4,154,247 A | 5/1979 | O'Neill |

(Continued)

FOREIGN PATENT DOCUMENTS

| | | |
|---|---|---|
| EP | 0 104 287 | 4/1984 |
| EP | 0 499 491 | 8/1992 |

(Continued)

OTHER PUBLICATIONS

W.A. Wesselink et al. "Analysis of Current Density and Related Parameters in Spinal Cord Stimulation," IEEE Transactions of Rehabilitating Engineering, vol. 6, pp. 200-207, Jun. 1998.

(Continued)

*Primary Examiner* — Christopher D Koharski
*Assistant Examiner* — Elizabeth K So

(57) ABSTRACT

Apparatus and techniques to address problems associated with lead migration, patient movement or position, histological changes, neural plasticity or disease progression. Disclosed are techniques for implanting a lead having therapy delivery elements, such as electrodes or drug delivery ports, within a vertebral or cranial bone so as to maintain these elements in a fixed position relative to a desired treatment site. The therapy delivery elements may thereafter be adjusted in situ with a position control mechanism and/or a position controller to improve the desired treatment, such as electrical stimulation and/or drug infusion to a precise target. The therapy delivery elements may be positioned laterally in any direction relative to the targeted treatment site or toward or away from the targeted treatment site. A control system maybe provided for open- or closed-loop feedback control of the position of the therapy delivery elements as well as other aspects of the treatment therapy.

13 Claims, 34 Drawing Sheets

(56) References Cited

U.S. PATENT DOCUMENTS

| | | |
|---|---|---|
| 4,166,469 A | 9/1979 | Littleford |
| 4,285,347 A | 8/1981 | Hess |
| 4,304,239 A | 12/1981 | Perlin |
| 4,351,330 A | 9/1982 | Scarberry |
| 4,374,527 A | 2/1983 | Iversen |
| 4,379,462 A | 4/1983 | Borkan |
| 4,414,986 A | 11/1983 | Dickhudt |
| 4,419,819 A | 12/1983 | Dickhudt |
| 4,519,403 A | 5/1985 | Dickhudt |
| 4,522,212 A | 6/1985 | Gelinas |
| 4,549,556 A | 10/1985 | Tarjan |
| 4,590,949 A | 5/1986 | Pohndorf |
| 4,640,298 A | 2/1987 | Pless |
| 4,658,835 A | 4/1987 | Pohndorf |
| 4,692,147 A | 9/1987 | Duggan |
| 4,699,147 A | 10/1987 | Chilson |
| 4,784,141 A * | 11/1988 | Peers-Trevarton ............... 607/37 |
| 4,800,898 A | 1/1989 | Hess |
| 4,989,617 A | 2/1991 | Memberg |
| 5,010,894 A | 4/1991 | Edhag |
| 5,056,532 A | 10/1991 | Hull |
| 5,113,859 A | 5/1992 | Funke |
| 5,117,828 A | 6/1992 | Metzger |
| 5,121,754 A | 6/1992 | Mullett |
| 5,143,067 A | 9/1992 | Rise |
| 5,203,770 A | 4/1993 | Wigness |
| 5,215,103 A | 6/1993 | Desai |
| 5,255,678 A | 10/1993 | Deslauriers |
| 5,259,387 A | 11/1993 | dePinto |
| 5,282,468 A | 2/1994 | Klepinski |
| 5,306,272 A | 4/1994 | Cohen |
| 5,344,439 A | 9/1994 | Otten |
| 5,365,926 A | 11/1994 | Desai |
| 5,370,679 A | 12/1994 | Atlee, III |
| 5,391,200 A | 2/1995 | KenKnight |
| 5,397,339 A | 3/1995 | Desai |
| 5,397,342 A | 3/1995 | Heil, Jr. |
| 5,409,453 A | 4/1995 | Lundquist |
| 5,411,025 A | 5/1995 | Webster, Jr. |
| 5,417,719 A | 5/1995 | Hull |
| 5,423,864 A | 6/1995 | Ljungstroem |
| 5,431,696 A | 7/1995 | Atlee, III |
| 5,458,629 A | 10/1995 | Baudino |
| 5,464,446 A | 11/1995 | Dreessen |
| 5,474,555 A | 12/1995 | Puno |
| 5,483,022 A | 1/1996 | Mar |
| 5,558,672 A | 9/1996 | Edwards |
| 5,562,670 A | 10/1996 | Branemark |
| 5,575,810 A | 11/1996 | Swanson |
| 5,634,462 A | 6/1997 | Tyler |
| 5,643,330 A | 7/1997 | Holsheimer |
| 5,662,108 A | 9/1997 | Budd |
| 5,683,422 A | 11/1997 | Rise |
| 5,702,429 A | 12/1997 | King |
| 5,702,438 A | 12/1997 | Avitall |
| 5,713,922 A | 2/1998 | King |
| 5,713,923 A | 2/1998 | Ward |
| 5,716,316 A | 2/1998 | Cartier |
| 5,716,377 A | 2/1998 | Rise |
| 5,733,322 A | 3/1998 | Starkebaum |
| 5,769,077 A | 6/1998 | Lindegren |
| 5,792,186 A | 8/1998 | Rise |
| 5,814,014 A | 9/1998 | Elsberry |
| 5,824,021 A | 10/1998 | Rise |
| 5,846,196 A | 12/1998 | Siekmeyer |
| 5,916,213 A | 6/1999 | Haissaguerre |
| 5,925,070 A | 7/1999 | King |
| 5,954,665 A | 9/1999 | Ben-Haim |
| 6,014,588 A | 1/2000 | Fitz |
| 6,053,920 A | 4/2000 | Carlsson |
| 6,059,750 A | 5/2000 | Fogarty et al. |
| 6,161,047 A | 12/2000 | King |
| 6,205,361 B1 | 3/2001 | Kuzma |
| 6,292,702 B1 | 9/2001 | King |
| 6,319,241 B1 | 11/2001 | King |
| 6,415,187 B1 | 7/2002 | Kuzma |
| 6,522,932 B1 | 2/2003 | Kuzma |
| 6,714,822 B2 | 3/2004 | King |
| 6,973,180 B1 * | 12/2005 | Kunisch et al. .......... 379/399.01 |
| 7,734,342 B2 * | 6/2010 | Gielen et al. ...................... 607/3 |
| 2001/0023367 A1 | 9/2001 | King |
| 2001/0053885 A1 | 12/2001 | Gielen |
| 2002/0151948 A1 | 10/2002 | King |

FOREIGN PATENT DOCUMENTS

| | | |
|---|---|---|
| WO | 93 04734 | 3/1993 |
| WO | 94 07413 | 4/1994 |
| WO | 96 34560 | 11/1996 |
| WO | 96 39932 | 12/1996 |
| WO | 97 32532 | 9/1997 |
| WO | 99 55411 | 11/1999 |

OTHER PUBLICATIONS

J. Holsheimer, et al., "Optimum Electrode Geometry for spinal Cord stimulation: The Narrow Bipole and Tripole," Medical & Biological Engineering & Computing, vol. 35, Sep. 1997, pp. 493-497.

J. Holsheimer et al., "MR Assessment of the Normal Position of the Spinal Cord in the Spinal Canal," Am. J. Neuroradiology, vol. 15, pp. 951-959 (1994).

Notification of Transmittal and PCT Search Report mailed Dec. 28, 1999 for International Application No. PCT/US99/08734 (Medtronic). (8 pages).

Form PCT/ISA/206 for International Application No. PCT/US99/08734 mailed Nov. 8, 1999 (5 pages).

* cited by examiner

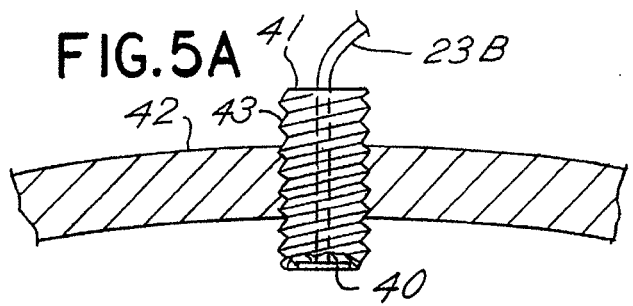
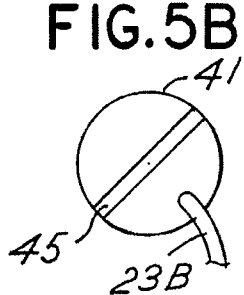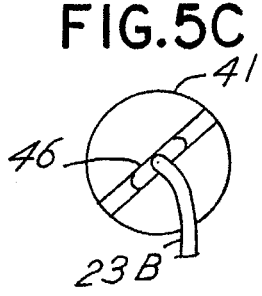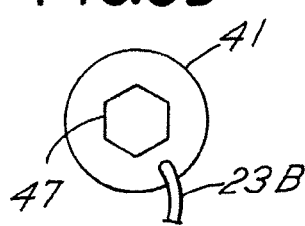
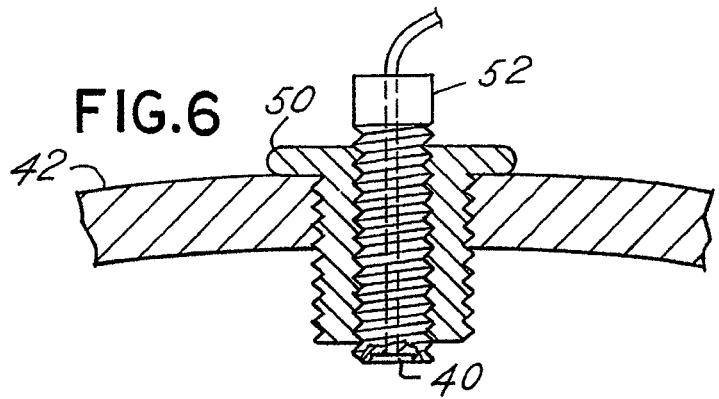
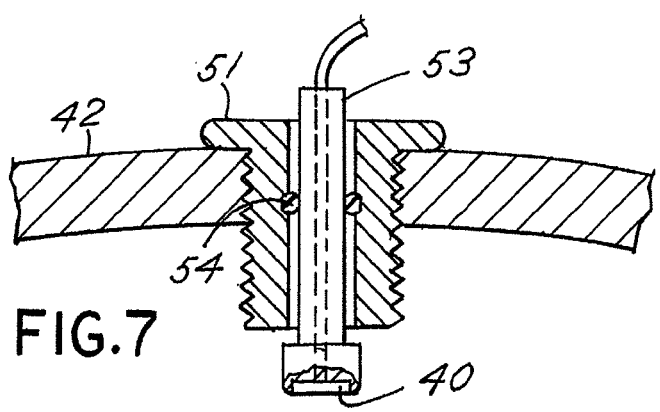

FIG.17D
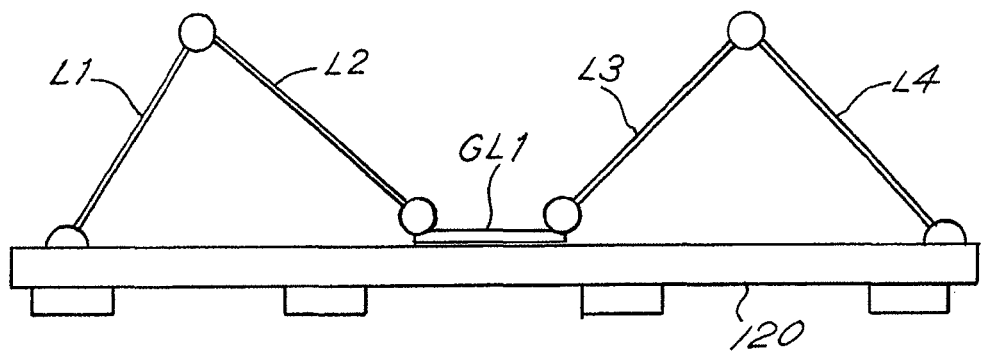
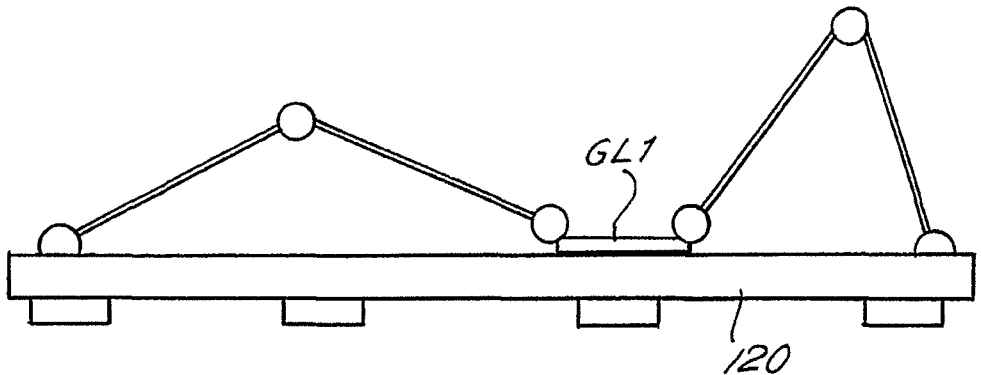
FIG.17E

FIG.22
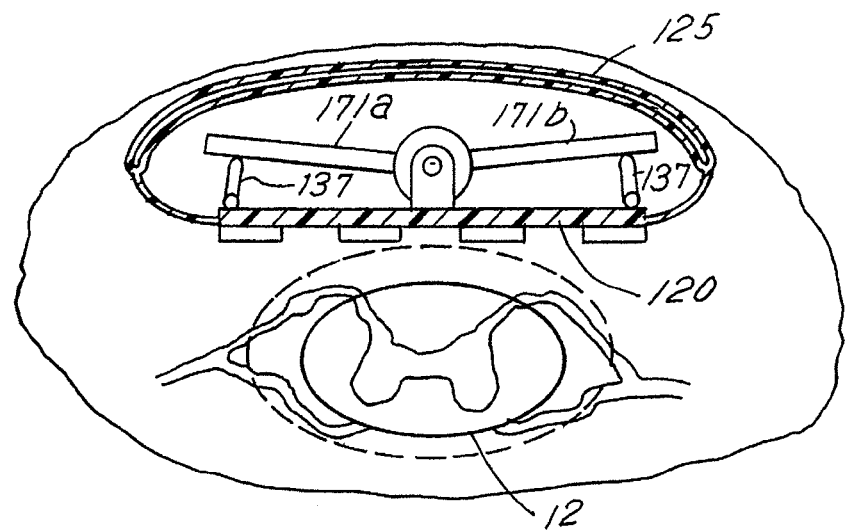
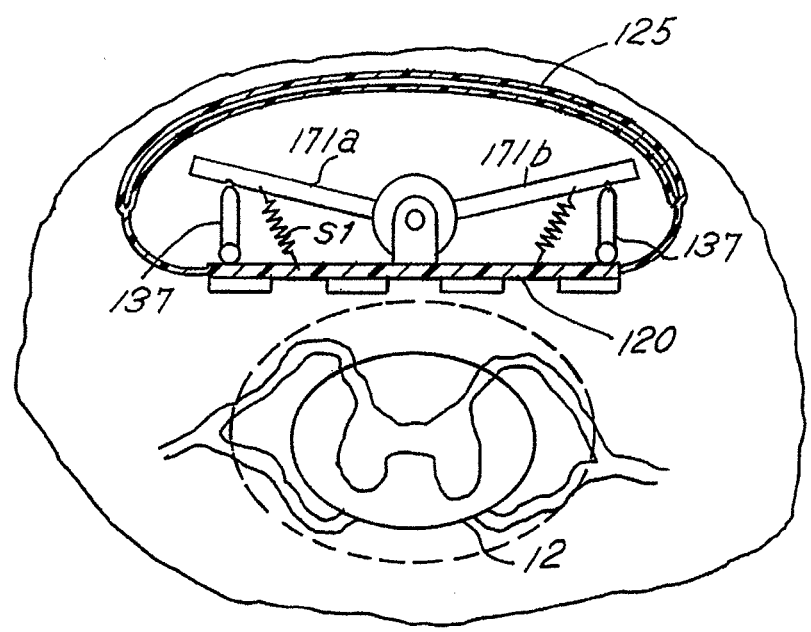
FIG.23

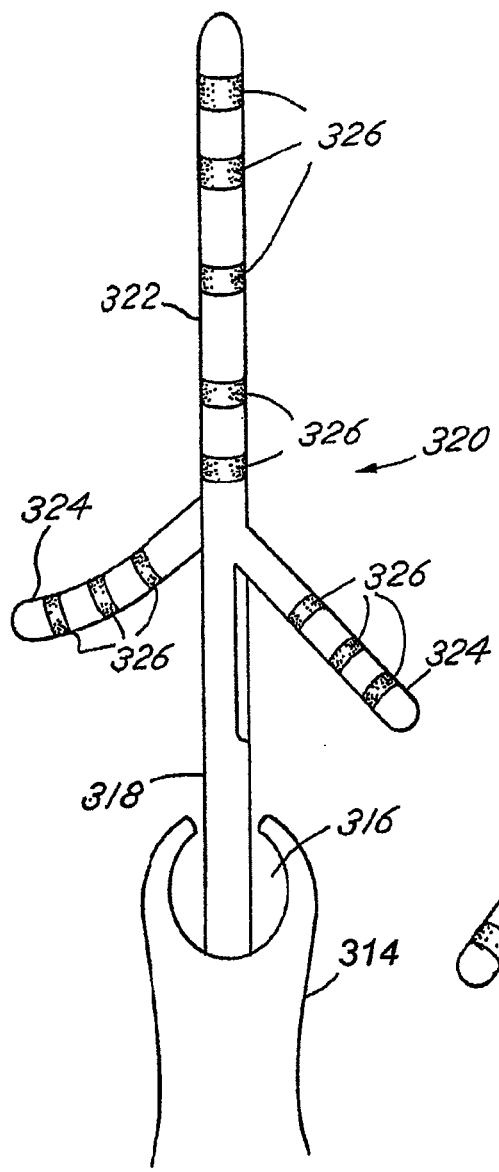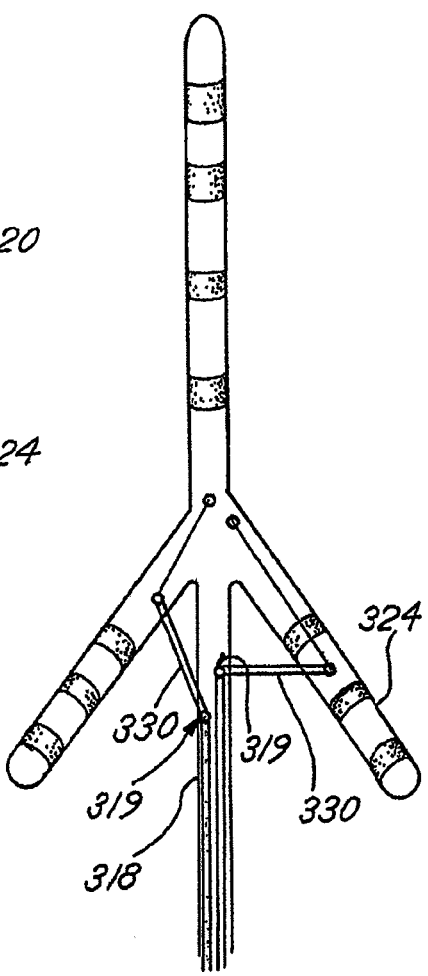
FIG.24
FIG.25

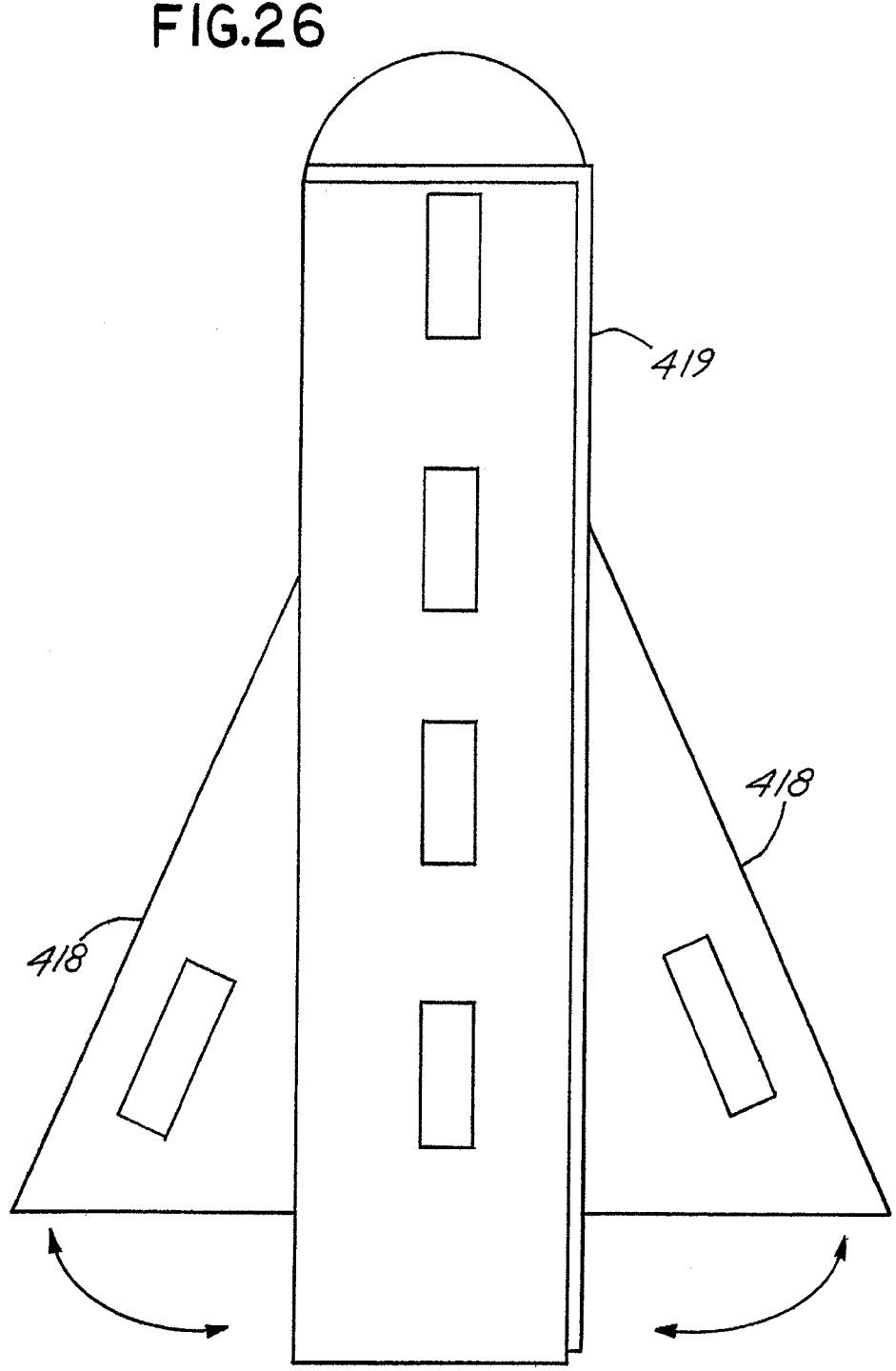

FIG. 27A
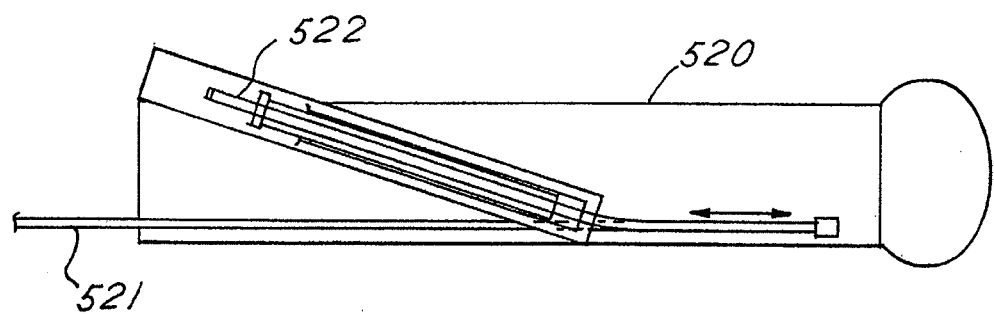
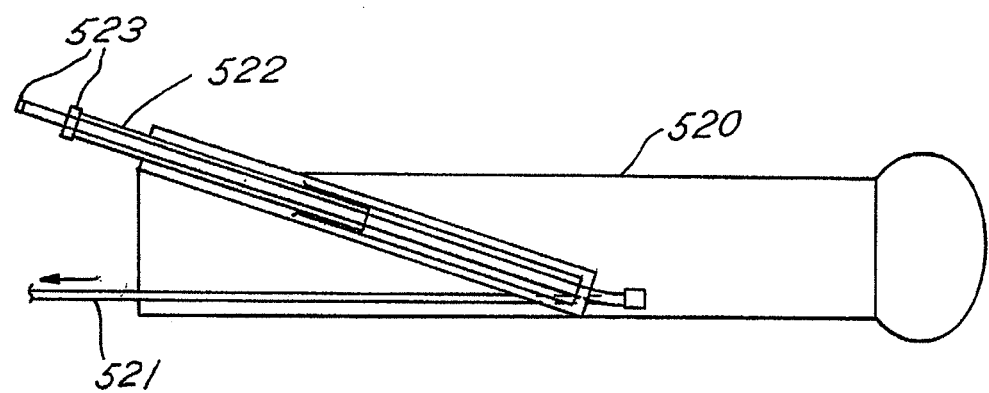
FIG. 27B

TRANSVERSE PROCESS
LAMINA
FACET
SPINOUS PROCESS

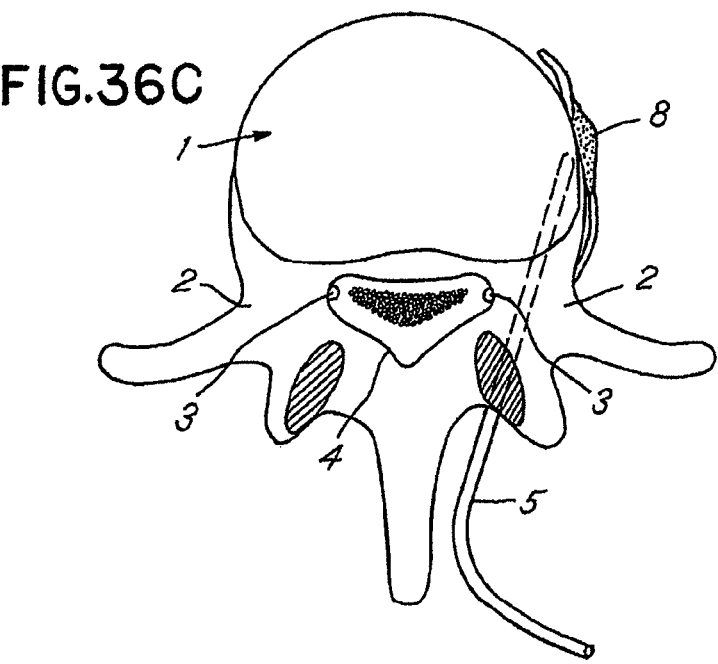
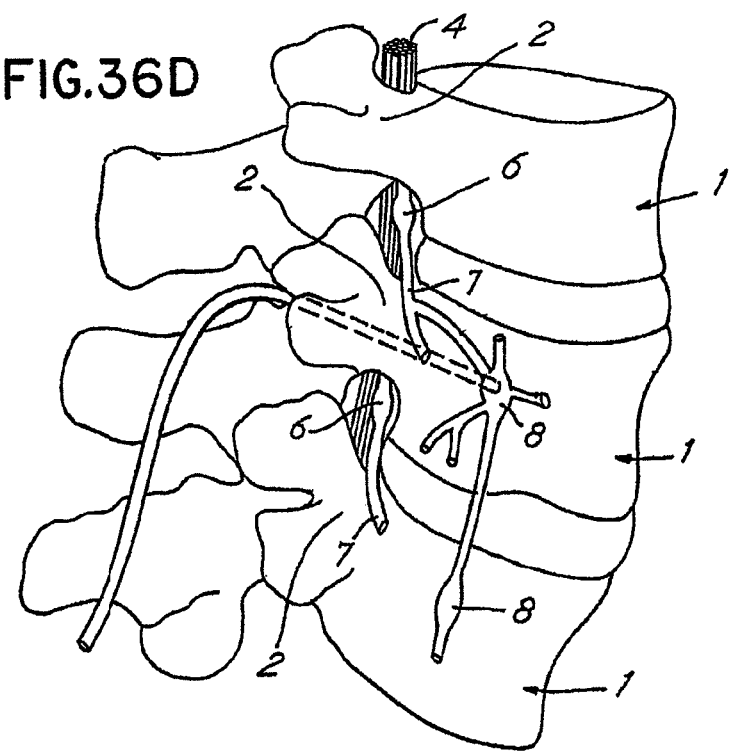

TECHNIQUES FOR POSITIONING THERAPY DELIVERY ELEMENTS WITHIN A SPINAL CORD OR BRAIN

RELATED APPLICATION

This is a continuation application of U.S. application Ser. No. 11/669,758 filed Jan. 31, 2007, now U.S. Pat. No. 7,734,342 issued Jun. 8, 2010, which is a continuation application of U.S. application Ser. No. 10/881,239 filed Jun. 30, 2004 now U.S. Pat. No. 7,191,018, which is a continuation application of U.S. application Ser. No. 09/934,001 filed Aug. 21, 2001, now U.S. Pat. No. 6,795,737 issued Sep. 21, 2004, which is a division of U.S. application Ser. No. 09/303,145 filed Apr. 30, 1999, now U.S. Pat. No. 6,319,241 issued Nov. 20, 2001, which is a continuation-in-part of the earlier filed patent application Ser. No. 09/070,136 entitled "Apparatus and Method for Expanding a Stimulation Lead Body in Situ," filed on Apr. 30, 1998, now U.S. Pat. No. 6,161,047 issued Dec. 12, 2000, for which priority is claimed. The above-identified applications are incorporated herein by reference in their entireties, and priority to the above-identified applications is claimed.

BACKGROUND OF THE INVENTION

The present invention relates to stimulation or drug delivery systems, and more particularly relates to techniques for positioning the treatment therapy elements, such as electrodes or catheters, to provide more effective treatment therapy.

FIELD OF THE INVENTION

Description of Related Art

Electrical stimulation techniques have become increasingly popular for treatment of pain and various neurological disorders. Typically, an electrical lead having one or more electrodes is implanted near a specific site in the brain or spinal cord of a patient. The lead is coupled to a signal generator which delivers electrical energy through the electrodes to nearby neurons and neural tissue. The electrical energy delivered through the electrodes creates an electrical field causing excitation of the nearby neurons to directly or indirectly treat the pain or neurological disorder.

Presently, only highly skilled and experienced practitioners are able to position a stimulation lead in such a way that the desired overlap between stimulation sites and target tissue is reached and desired results are obtained over time with minimal side effects. It requires much time and effort to focus the stimulation on the desired body region during surgery. These leads cannot be moved by the physician without requiring a second surgery.

The major practical problem with these systems is that even if the paresthesia (sensation of stimulation) location covers the pain area perfectly during surgery, the required paresthesia pattern often changes later due to lead migration, histological changes (such as the growth of connective tissue around the stimulation electrode), neural plasticity or disease progression. As a result, the electrical energy may stimulate undesired portions of the brain or spinal cord.

Maintaining the lead in a fixed position and in proximity to the treatment site is therefore highly desirable. Presently known systems are susceptible to lead migration. Accordingly, the lead may migrate such that the targeted tissue is outside of the effective steerable treatment range of the lead. Additionally, for some treatment applications, the lead just cannot be placed optimally to provide the desired treatment therapy. For example, in the case of treatment of lower back pain, electrical stimulation may be provided at the middle thoracic vertebral segments, T6-T9. With currently available systems, this often fails mostly due to the great thickness of the cerebral spinal fluid (CSF) layer.

Alternatively, it is desirable to redirect paresthesia without requiring a second surgery to account for lead migration, histological changes, neural plasticity or disease progression. With present single channel approaches, however, it is difficult to redirect paresthesia afterwards, even though limited readjustments can be made by selecting a different contact combination, pulse rate, pulse width or voltage. These problems are found not only with spinal cord stimulation (SCS), but also with peripheral nerve stimulation (PNS), depth brain stimulation (DBS), cortical stimulation and also muscle or cardiac stimulation. Similar problems and limitations are present in drug infusion systems.

Recent advances in this technology have allowed the treating physician or the patient to steer the electrical energy delivered by the electrodes once they have been implanted within the patient. For example, U.S. Pat. No. 5,713,922 entitled "Techniques for Adjusting the Locus of Excitation of Neural Tissue in the Spinal Cord or Brain," issued on Feb. 3, 1998 to and assigned to Medtronic, Inc. discloses one such example of a steerable electrical energy. Other techniques are disclosed in application Ser. No. 08/814,432 (filed Mar. 10, 1997) and Ser. No. 09/024,162 (filed Feb. 17, 1998). Changing the electric field distribution changes the distribution of neurons recruited during a stimulus output, and thus provides the treating physician or the patient the opportunity to alter the physiological response to the stimulation. The steerability of the electric field allows the user to selectively activate different groups of nerve cells without physically moving the lead or electrodes.

These systems, however, are limiting in that the steerable electric field is limited by the location of the electrodes. If the electrodes move outside of the desired treatment area or if the desired stimulation area is different due to histological changes or disease migration, the desired treatment area may not be reached even by these steerable electrodes. Further, even if these steerable electrodes may be able to stimulate the desired neural tissue, the distance from the electrodes to the tissue may be too large such that it would require greater electrical power to provide the desired therapy. It has been shown that only a fraction of the current from modern stimulation devices gets to the neurons of interest. See W. A. Wesselink et al. "Analysis of Current Density and Related Parameters in Spinal Cord Stimulation," IEEE Transactions on Rehabilitation Engineering, Vol. 6, pp. 200-207 (1998). This not only more rapidly depletes the energy reserve, but it also may stimulate undesired neural tissue areas thereby creating undesired side effects such as pain, motor affects or discomfort to the patient.

In short, there remains a need in the art to provide an electrical stimulation device that is not susceptible to lead migration and that may be positioned in proximity to the treatment site. In addition, there remains a need in the art to provide an electrical stimulation device that may be adjusted to account for lead migration, patient movement or position, histological changes, and disease migration.

SUMMARY OF THE INVENTION

As explained in more detail below, the present invention overcomes the above-noted and other shortcomings of known electrical stimulation and drug delivery techniques. The present invention provides a technique for positioning therapy delivery elements, such as electrodes and/or catheters, optimally closer to the desired treatment area. The present invention includes a therapy delivery device such as a signal generator or a drug pump, at least one lead having at least one therapy delivery element coupled to the therapy delivery device and at least one position control mechanism coupled to the therapy delivery elements for adjusting the position of the therapy delivery element relative to the excitable tissue of interest. The position may be adjusted laterally in any number of directions relative to the lead or toward or away from the excitable tissue of interest. Any number of position control mechanisms may be incorporated to selectively adjust the position of the therapy delivery elements. Also, a position controller such as a microprocessor may be utilized to operate the position control mechanism to position the therapy delivery elements.

In other embodiments of the present invention, one or more of therapy delivery elements may be placed within the cranial or vertebral bone of the patient so as to maintain the therapy delivery elements in a fixed position relative to the targeted neural tissue. The therapy delivery elements may thereafter be adjusted with a position control mechanism and/or a position controller to improve the desired treatment therapy.

By using the foregoing techniques, therapy delivery elements may be positioned to provide treatment therapy such as electrical stimulation and/or drug infusion to a precise target. Additionally, the present invention accounts for the problems associated with lead migration, histological changes, neural plasticity or disease progression.

Optionally, the present invention may incorporate a closed-loop system which may automatically adjust (1) the positioning of the therapy delivery elements in response to a sensed condition of the body such as a response to the treatment therapy; and/or (2) the treatment therapy parameters in response to a sensed symptom or an important related symptom indicative of the extent of the disorder being treated.

Examples of the more important features of this invention have been broadly outlined above so that the detailed description that follows may be better understood and so that contributions which this invention provides to the art may be better appreciated. There are, of course, additional features of the invention which will be described herein and which will be included within the subject matter of the claims appended hereto.

BRIEF DESCRIPTION OF THE DRAWINGS

These and other advantages and features of the invention will become apparent upon reading the following detailed description and referring to the accompanying drawings in which like numbers refer to like parts throughout and in which:

FIGS. 5A-D disclose embodiments of the present invention where electrodes are anchored within vertebral bones of the spinal cord;

FIG. 6 discloses another embodiment of the present invention having a collar screwed into vertebral bone;

FIG. 7 discloses another embodiment of the present invention having a collar with an "O" ring to hold an electrode housing in position by pressure;

FIGS. 17A-E disclose other embodiments whereby a portion of the lead body thickness is adjusted using gliders;

FIGS. 22 and 23 illustrate embodiments of the present invention where more than one of the elements of the above figures above are implemented;

FIG. 24 illustrates yet another embodiment of a lead having two spans extending laterally from its body;

FIG. 25 illustrates yet another embodiment of a lead having two spans that are adjustable by use of guide struts;

FIG. 26 discloses an embodiment of a paddle lead having movable lateral spans;

FIGS. 27A-B disclose yet another embodiment of a paddle lead capable of extending electrodes laterally;

FIGS. 36A-D illustrate other embodiments of a lead being implanted within a vertebral bone of a patient;

DESCRIPTION OF THE PREFERRED EMBODIMENTS

Figure 1:
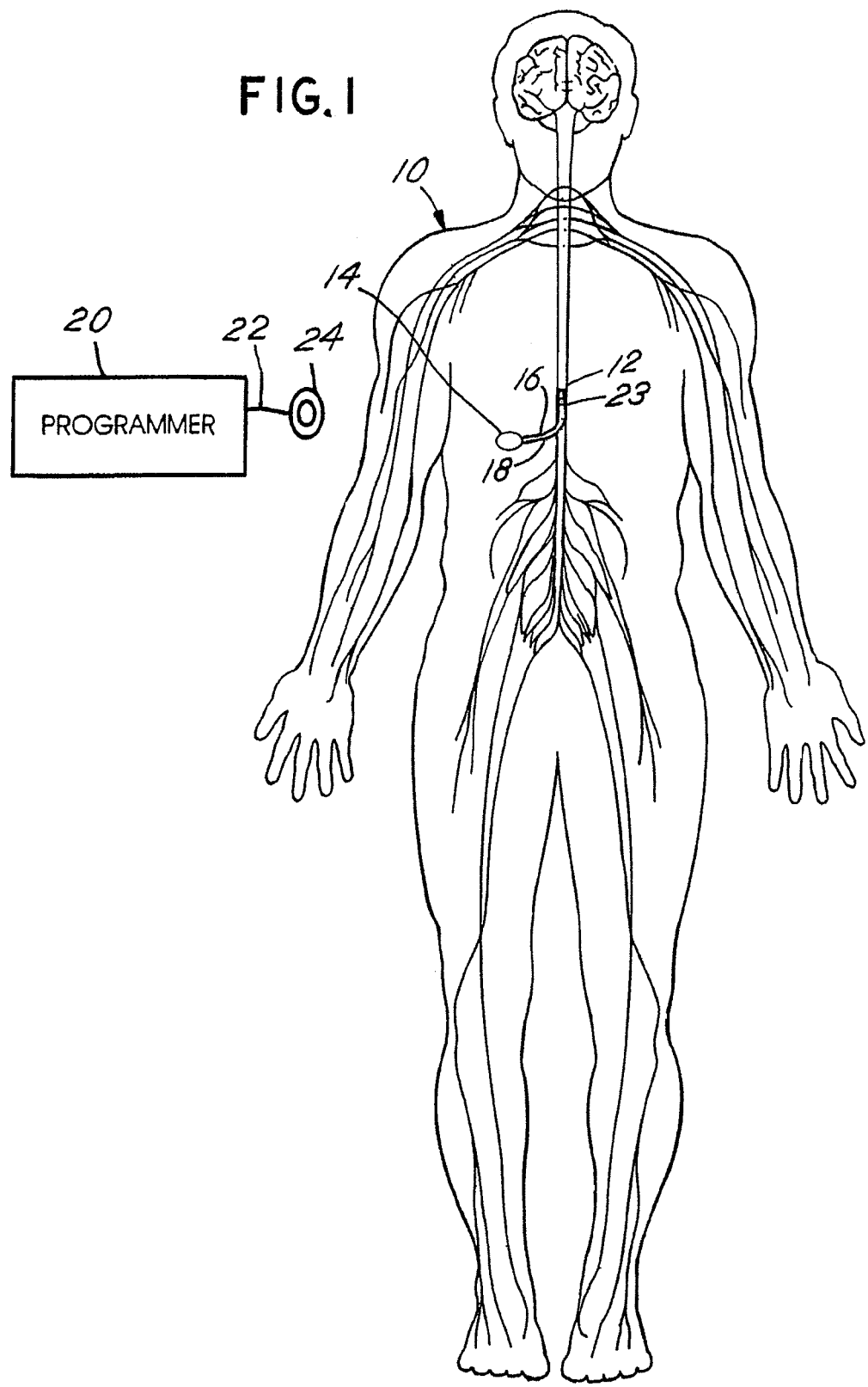
FIG. 1 depicts a neurostimulation device in accordance with an embodiment of the present invention.

FIG. 1 depicts a neurostimulation therapy delivery device 14 in accordance with an embodiment of the present invention. Therapy delivery device 14 made in accordance with the preferred embodiment is preferably implanted below the skin of a patient or, alternatively, may be an external device. Therapy delivery device 14 may be implanted as shown in FIG. 1, in the abdomen or any other portion of the body 10. One or more leads 23 are positioned to stimulate a specific site in a spinal cord 12. Therapy delivery device 14 may take the form of a modified signal generator Model 7424 manufactured by Medtronic, Inc. under the trademark Itrel II which is incorporated by reference in its entirety. Lead 23 may take the form of any of the leads sold with the Model 7424, for stimulating a spinal cord, and is coupled to therapy delivery device 14 by one or more conventional conductors 16 and 18. Lead 23 may include a paddle lead, a lead having one or more therapy delivery devices such as stimulation electrodes and/or catheters, or a combination catheter/lead capable of providing electrical stimulation and drug delivery. Lead 23 may also have recording electrodes. Exemplary embodiments of lead 23 incorporating the principles of the present invention are shown in the figures of the present application and discussed herein.

As shown in FIG. 1, the distal end of lead 23 terminates in one or more therapy delivery elements such as stimulation electrodes generally implanted into or near a selected portion of the spinal cord by conventional surgical techniques. The location of the electrodes is determined by the type of treatment that is desired. Any number of electrodes may be used for various applications. Each of the electrodes are preferably individually connected to therapy delivery device 14 through lead 23 and conductors 16 and 18. Lead 23 is surgically implanted either by a laminotomy or by a percuntaneous needle.

Therapy delivery device or signal generator 14 may programmed to provide a predetermined stimulation dosage in terms of pulse amplitude, pulse width, pulse frequency, or duty cycle. As preferred, a programmer 20 may be utilized to provide stimulation parameters to therapy delivery device 14 via telemetry. Programmer is coupled to an antenna 24 via conductor 22.

The system may optionally include one or more sensors to provide closed-loop feedback control of the treatment therapy and/or electrode positioning. One or more sensors are attached to or implanted into a portion of a patient's body suitable for detecting a physical and/or chemical symptom or an important related symptom of the body. The feedback aspect of the present invention is discussed in further detail herein.

Although the invention will be described herein with reference to spinal cord stimulation (SCS) procedures, Cortical Surface Stimulation, and or Deep Brain Stimulation (DBS) it will be recognized that the invention finds utility in applications other than SCS procedures, including other applications such as Peripheral Nerve or Ganglia Stimulation, Intra-Spinal Stimulation, Sacral Root Stimulation, or Intraventricular Cerebral Stimulation. In addition, the invention finds applicability to SCS procedures where the lead is placed in the intrathecal or subdural space. The present invention may also be utilized to provide stimulation of various muscles of the body such as the cardiac muscle. The invention also finds utility to drug therapy where electrical components are replaced with conduits and catheters for conducting drug material to the therapy site. In this case, especially, the lead may be placed in the intrathecal or subdural space.

Figure 2:
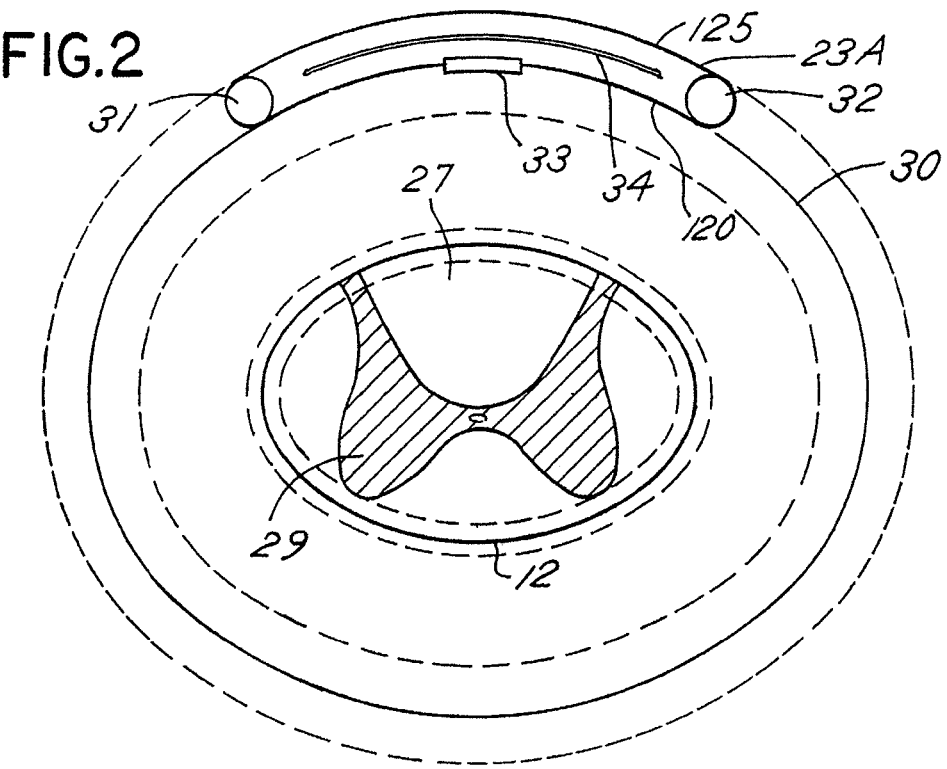
FIG. 2 is a cross-sectional view of spinal cord at spinal bone level T-6 having an implanted lead in accordance with a preferred embodiment of the present invention.

FIG. 2 is a cross-sectional view of spinal cord 12 at spinal bone level T-6 having an implanted lead 23A in accordance with a preferred embodiment of the present invention. Spinal cord 12 generally includes white matter 27, grey matter 29, and a surrounding dural sack 30. As shown, lead 23A is implanted in the epidural space outside of dural sack 30, but may alternatively be implanted in intrathecal spinal space or subcortically beneath dura 30. Lead 23A has a curved shape to match the shape of dura 30. The curvature may be matched to each spinal level or may be a general shape to approximately match all levels of spinal cord. Alternatively, lead 23A may be flat such that it "grips" the vertebral bone on its dorsal edges and is less prone to migration or rotation. Lead 23A has a dorsal side 125 away from spinal cord 12 and a ventral side 120 facing spinal cord 12.

Figure 3:
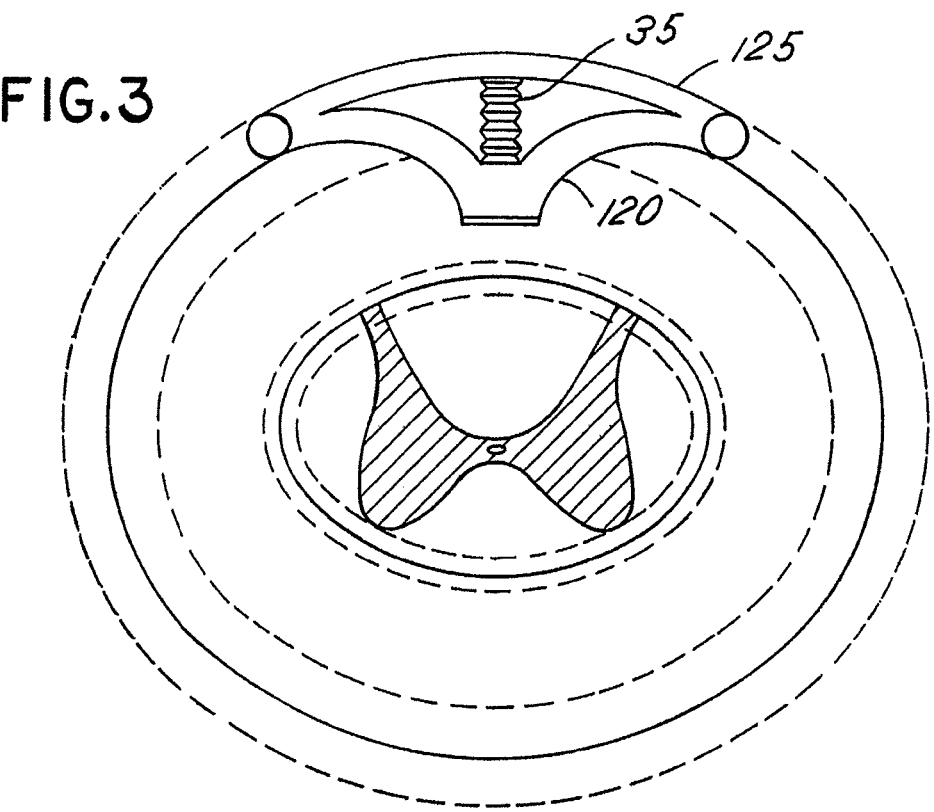
FIG. 3 illustrates a position controller having metal bellows.
Figure 4:
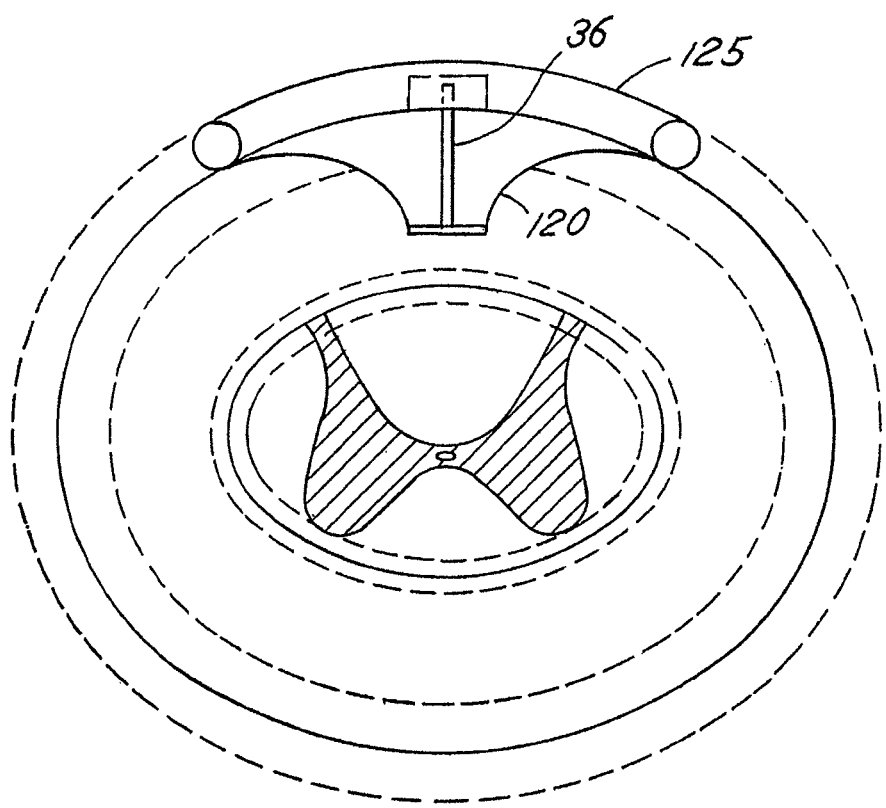
FIG. 4 illustrates a position controller having a piston.

FIGS. 2-4 show the average width, height and spacing of tissue components at vertebral bone level T6. The dashed lines in these figures indicate distances of one standard deviation from the mean. See J. Holsheimer et al., "MR Assessment of the Normal Position of the Spinal Cord in the Spinal Cannal," Am. J. Neuroradiology, Vol. 15, pp. 951-959 (1994).

Referring still to FIG. 2, lead 23A has two lateral electrode contacts 31 and 32 at opposite ends of lead 23A and a central electrode contact 33 in the central portion of lead 23A. Lateral and central electrodes 31-33 may be anodes, cathodes or nonactive. Alternatively, any one or more of lateral and central electrodes 31-33 may be recording electrodes or drug delivery ports. Lead 23A is preferably able to control the dorsal cerebral spinal fluid (CSF) width, even though it is placed outside of dura. In accordance with the present invention, lead 23A includes a position control mechanism capable of adjusting the position of one or more of the lateral or central electrodes 31-33. As shown, central electrode 33 is at a maximal distance dorsally from spinal cord 12. A position control mechanism may adjust the distance between central electrode 33 and the spinal cord 12. In the embodiment of FIG. 2, the position control mechanism is in the form of a cavity 34 within lead 23A which is able to expand and fill with fluid (controlled by a pump (not shown)) or other matter in the epidural space to reduce the separation between central electrode 33 and spinal cord 12. A pump (not shown) may be powered by signal generator 14 that also provides the stimulation energy for the electrodes at lateral and central electrodes 31-33 and a signal for controlling the position control mechanism. Alternatively, position control mechanism may be adjusted using external means and power such as a magnetic signal, a percutaneous needle or bulb on another component that can be pushed. Advantageously, central electrode 33 may be positioned such that the targeted neural tissue is stimulated with optimal efficacy and minimal side effects.

As shown in FIGS. 3 and 4, the position control mechanism may take any number of embodiments for allowing movement of the electrodes and holding the electrodes in position. FIG. 3 illustrates a position control mechanism having metal bellows 35 and FIG. 4 illustrates a position control mechanism having a piston 36. The bellows 35 of FIG. 3 may alternatively be a threaded rod. A spring may be added to return the electrode to a less extended position.

Further, the position control mechanism may control all or a selective group of electrodes. For example, one position control mechanism may control a longitudinal or transverse row of electrodes. Alternatively, each electrode to be adjusted may have its own individual position control mechanism.

The position control mechanism of the above embodiments is preferably controlled by a position controller which is discussed in further detail herein. The position control mechanism is preferably adjustable such that it does not unduly depress neural tissue or hinder blood flow. Sensing feedback may be utilized, for example by a mechanical measure within a lead or an ultrasound or other sensor to give information about the distance. Sensing feedback may also be utilized to automatically adjust the positioning of the electrodes to provide optimum treatment therapy. Sensing feedback is discussed in further detail herein.

FIGS. 5-9 disclose another group of embodiments of the present invention where electrodes are anchored to vertebral bones of the spinal cord. Alternatively, the electrodes may be implanted in the cortical bone of the skull. Electrodes may be positioned by drilling one or more holes at preselected locations in the bone. Leads having one or more electrodes may then be passed through the holes and positioned inside the vertebral canal/skull at optimal locations or distances from the target neural tissue. Electrodes may then be selectively adjusted in position after the implant. The depth of the electrodes may then be adjusted to provide the optimal stimulation therapy.

As shown in FIG. 5A, an electrode 40 at the end of a threaded housing 43 is provided by drilling housing 43 into bone 42 surrounding spinal cord 12. For dorsal column stimulation, bone 42 is preferably the dorsal aspect of vertebral bone. The lead 23B is coupled to electrode 40 and extends out through a top portion 41 of threaded housing 43. FIGS. 5B-D illustrates exemplary embodiments of the top portion of housing 41 to allow for engagement of various turning devices. FIG. 5B depicts a cavity 45 to provide engagement of a screwdriver-like device to turn housing 43 to adjust position of electrode 40 relative to spinal cord 12. FIG. 5C depicts a similar device but providing engagement of a slotted screwdriver-like device and showing lead 23B extending out through top portion 41 at point 46. FIG. 5D depicts a hexagonal cavity 47 for engagement of a hexagonal wrench-like device or percutaneous needle. Housing 43 preferably is threaded with a high pitch so that a relatively small turn provides relatively larger positioning of electrode 40 relative to the spinal cord 12. This minimizes the problem of lead 23B wrapping around housing 43.

FIG. 6 discloses another embodiment of the present invention having a collar 50 screwed into bone 42. An inner housing 52 similar to the housing 43 of FIG. 5 may be used to move electrode 40 relative to collar 50. This embodiment allows adjustment of electrode 40 at times after the system has been implanted and is less affected by growth of tissue over housing 52 and collar 51 to limit subsequent turning of housing 52 relative to collar 51. FIG. 7 discloses another embodiment where the collar 50 has an "O" ring 54 to hold housing 53 in position by pressure. Other means to lock housing 53 in position are also possible.

Figure 8:
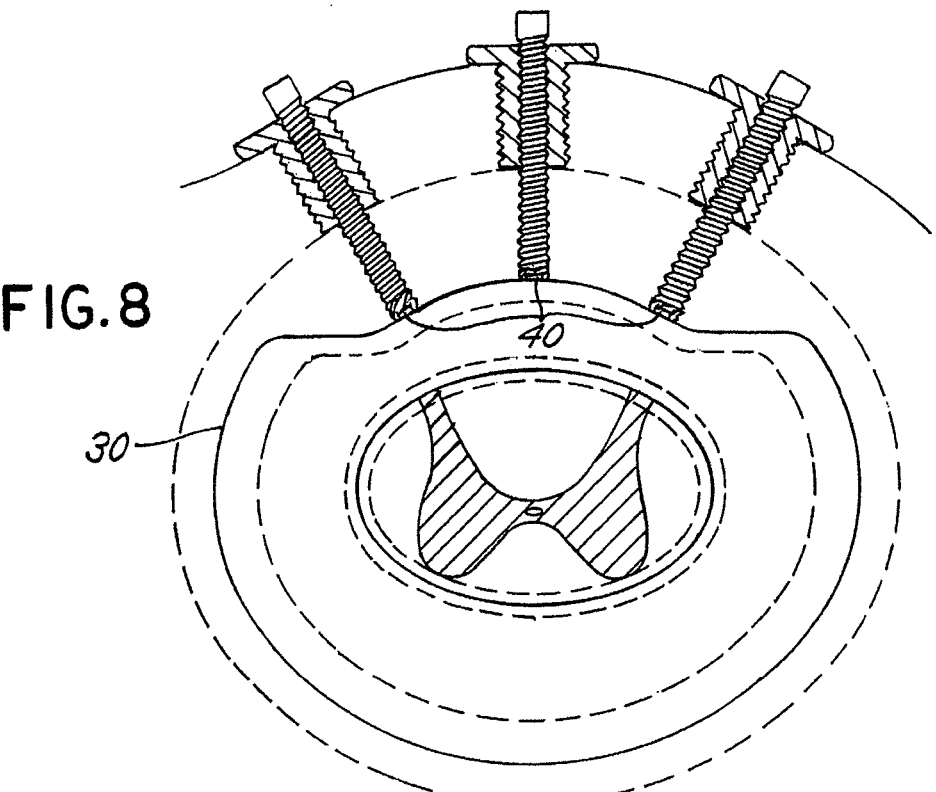
FIGS. 8 and 9 disclose other embodiments of the present invention where a plurality of electrodes are anchored through vertebral bones of the spinal cord.
Figure 9:
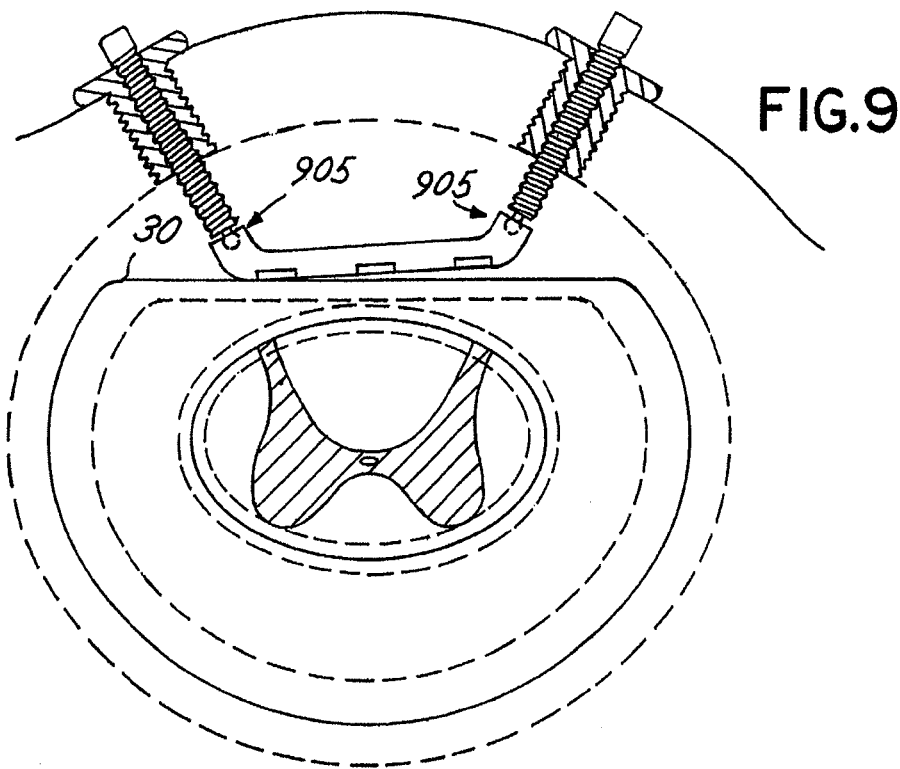

As shown in FIGS. 8 and 9, a plurality of electrodes may be provided than can be selectively or collectively adjusted relative to spinal cord 12. These electrodes may also be provided in a three-dimensional configuration along spinal cord 12. Further, though electrodes may be positioned closer to spinal cord 12, they preferably do not break the dural sack 30 to avoid leakage of CSF. FIG. 9 shows a ball and socket 905 or other swivel mechanism to allow turning of housing but not lead. Advantageously, placement of the lead through the vertebral bone avoids the problem of lead migration.

Figure 36A:
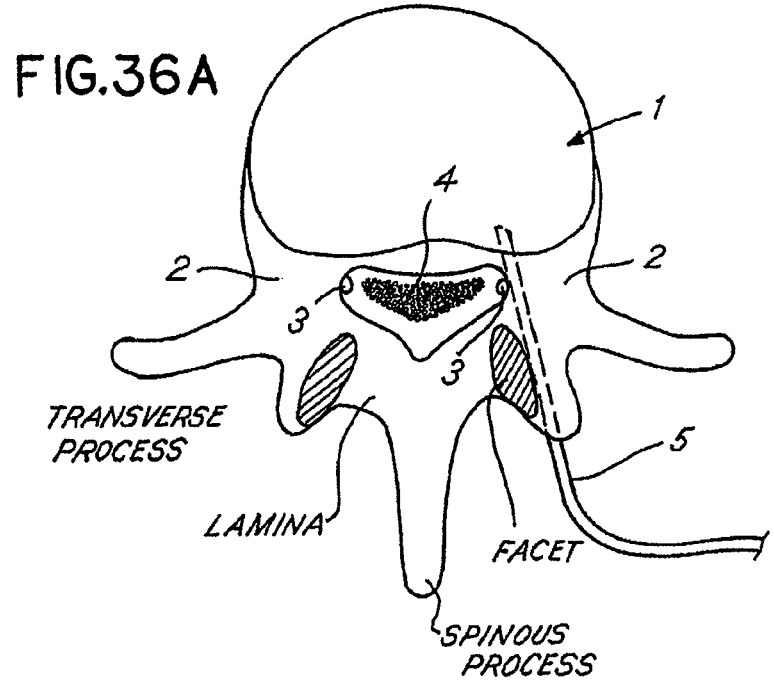
Figure 36B:
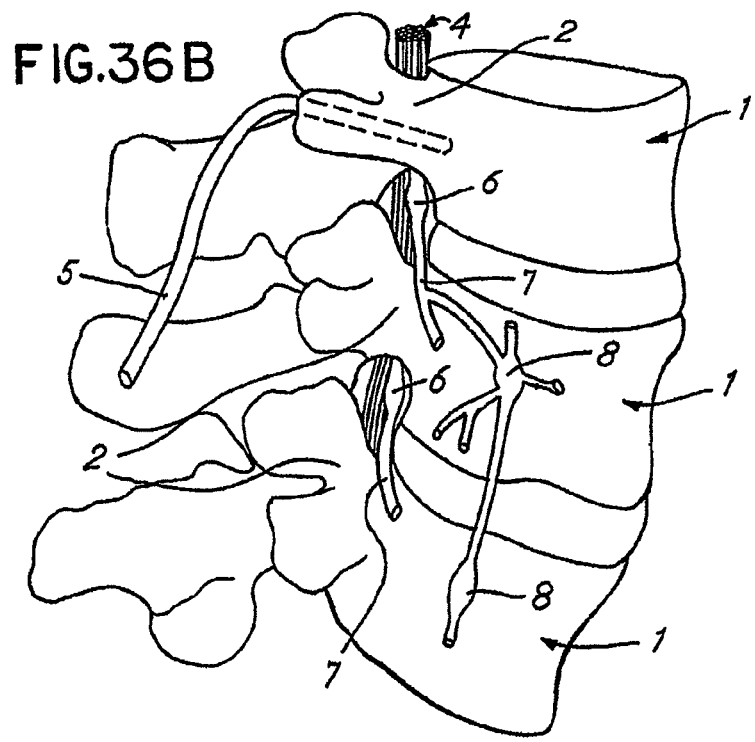

Alternatively, the lead may be implanted into the bone, as opposed to implant all the way through the bone, as illustrated in FIGS. 36A-D. For example, FIG. 36A depicts a lead 5 implanted into the bony aspects of the vertebral body. The lumbar spine is shown with the lead inserted into the pedicle 2 of the vertebral body 1 to stimulate nerve roots, particularly as the nerve roots 3 exit the spinal foramen 4. The lead 5 is implanted by drilling a hole through the pedicle 2 (from the posterior) and into the vertebral body. The lead 5 may then be inserted into the hole and fed to the end. Once in position, the lead 5 may be anchored at the posterior, bone entrance site using, for example, a burr cap. By keeping the lead hole medial and centered, the nerve roots can be stimulated. The specific target nerve site may be selected by varying the placement of the lead relative to the vertebral bone. FIG. 36B shows an isometric drawing of pedicular placement for stimulation of the nerve root as it exits the spinal foramen 4. Lead 5 is inserted into in the inferior portion of the vertebral pedicle 2 of the vertebral segment to enable stimulation of the dorsal root ganglion 6. By way of another example, in FIG. 36C, a lead 5 placed in the superior lateral portion of the vertebral bone will enable stimulation of the spinal nerve 7 of the segment superior. Advantageously, lead 5 may be placed so as to target desired neural tissue and avoid other tissue. In addition, lead 5 is anchored within the vertebral bone, thereby avoiding the risk of lead migration and avoiding compression of nerve tissue common in known techniques.

In addition, lead 5 may be implanted in any other bone areas that are proximal to targeted neural tissue. An example of placement to target other neural tissue is illustrated in FIG. 36C. This Figure illustrates placement for stimulation of the ganglia (8) of the sympathetic trunk. The hole for lead 5 is angled more lateral and made deeper up to the wall of the vertebral body 1. FIG. 36D is an isometric view of the same lead placement shown in FIG. 36C. The hole in the vertebrae begins at the posterior and is extended down the pedicle 2, into the vertebral body 1, toward the ganglion 8, but not through the wall of the vertebral body. This method allows stimulation of deep tissues without disrupting soft tissue. Again the lead could be anchored in the posterior bone by a burr hole cap or other means. Lead 5 of FIGS. 36A-D may be adjustable similar to those of FIGS. 5-9.

Figure 38A:
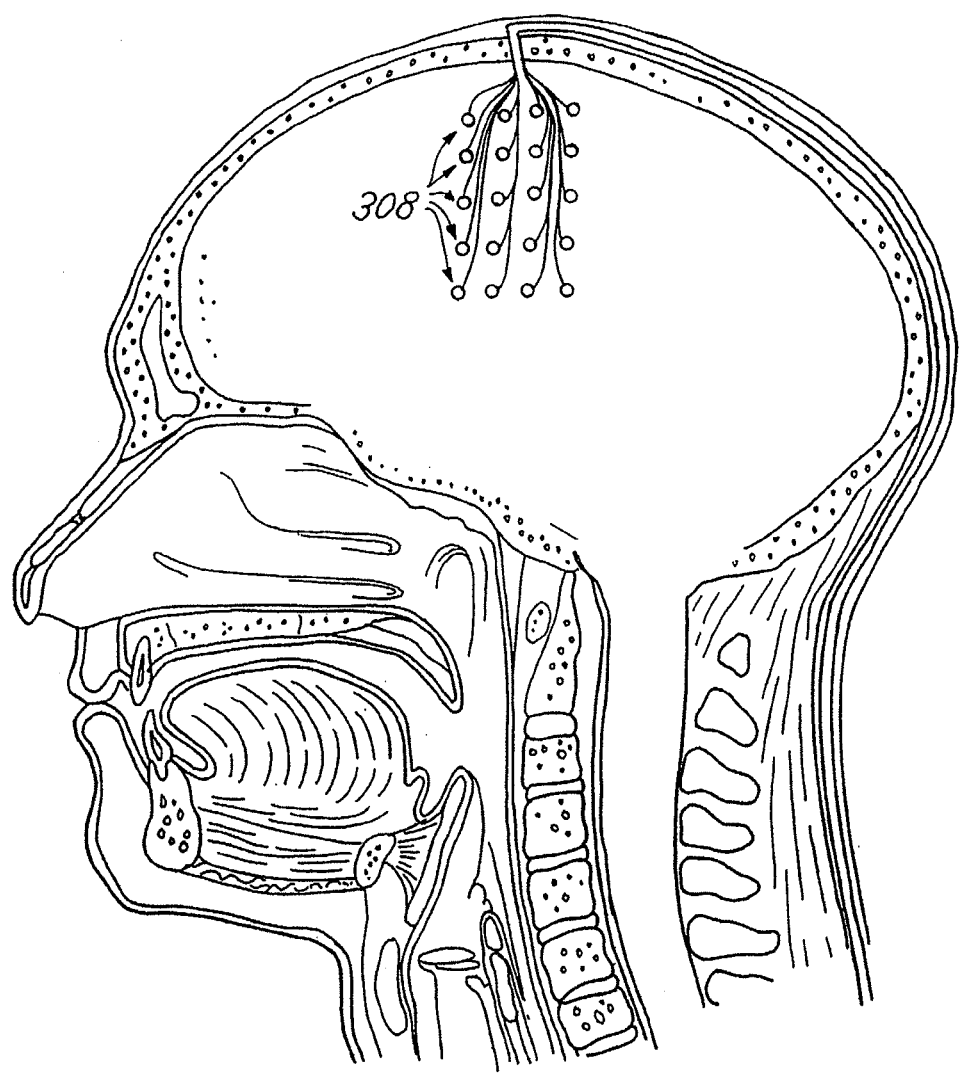
FIGS. 38A-C illustrate an embodiment of the present invention wherein a plurality of MCE's are implanted within the skull of a patient.
Figure 38B:
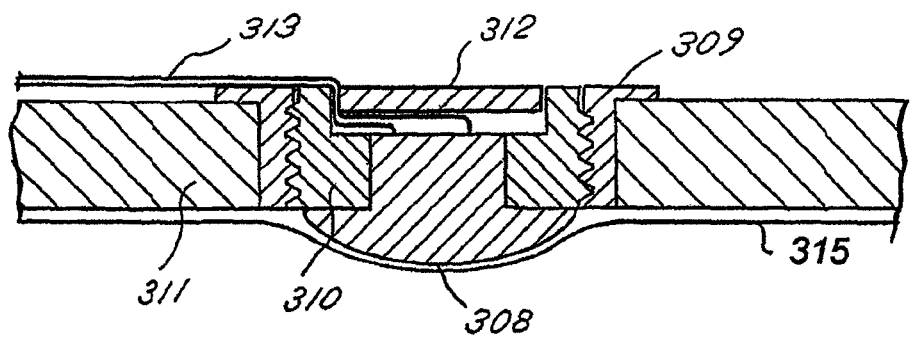
Figure 38C:
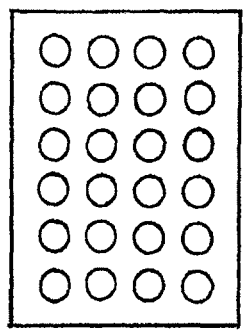

The advantages of fixing a lead to a vertebral bone may also be implemented in Cortical Brain Stimulation applications. FIG. 38A discloses another embodiment where one or more motor cortex electrodes (MCE) 308 are implanted into the skull of a patient for stimulation and/or recording of the cortex via contact with the dura. As shown in FIG. 38B, MCE 308 may be screwed using a burr hole ring 309 and screw 310 within the skull 311 of a patient using known techniques. Advantageously, the present embodiment enables several MCEs 308 to be placed to allow flexibility in choosing the best stimulation. A MCE targeting grid (FIG. 38C) could be constructed of a material such as, for example, $CuSO_4$, so that the hole locations are visible under magnetic resonance imaging (MRI). Placement of the MCE 308 within the skull 311 allows for more accurate placement of the MCEs 308 and avoids the problem of lead migration. In addition, screw 310, referring to FIG. 38B, can be advanced or retracted to ensure an optimal contact between the electrode 308 and dura 315 to maximize stimulation effect while minimizing mechanical deformation of dura and cortex. Further, less invasive surgical procedure is required, thereby minimizing the risk of damage to the dura 315. Such a configuration of MCEs 308 may be used for cortex stimulation for any number of disorders, including but not limited to, pain, epilepsy, anxiety/physiological disorders, and movement disorders.

Figure 10:
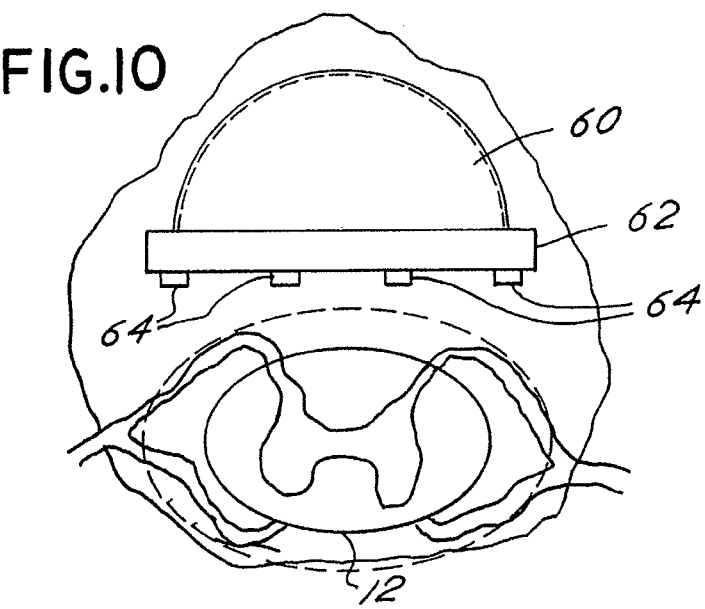
FIG. 10 discloses another embodiment of the present invention where a balloon is implemented on a dorsal side of a paddle lead.
Figure 12A:
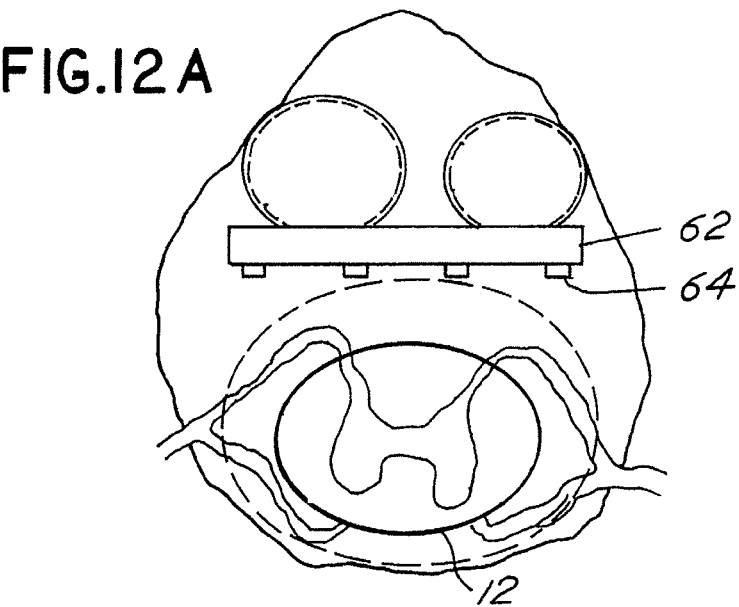
FIGS. 12A-B depict other embodiments wherein a plurality of balloons are implemented to allow more selective adjustment of the electrodes relative to the spinal cord.
Figure 12B:
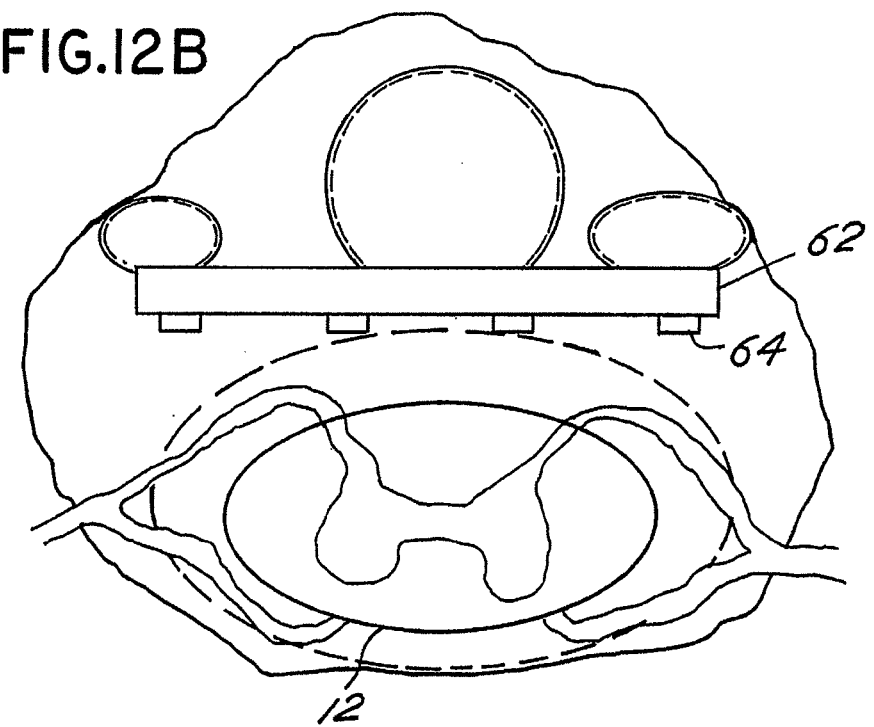
Figure 13A:
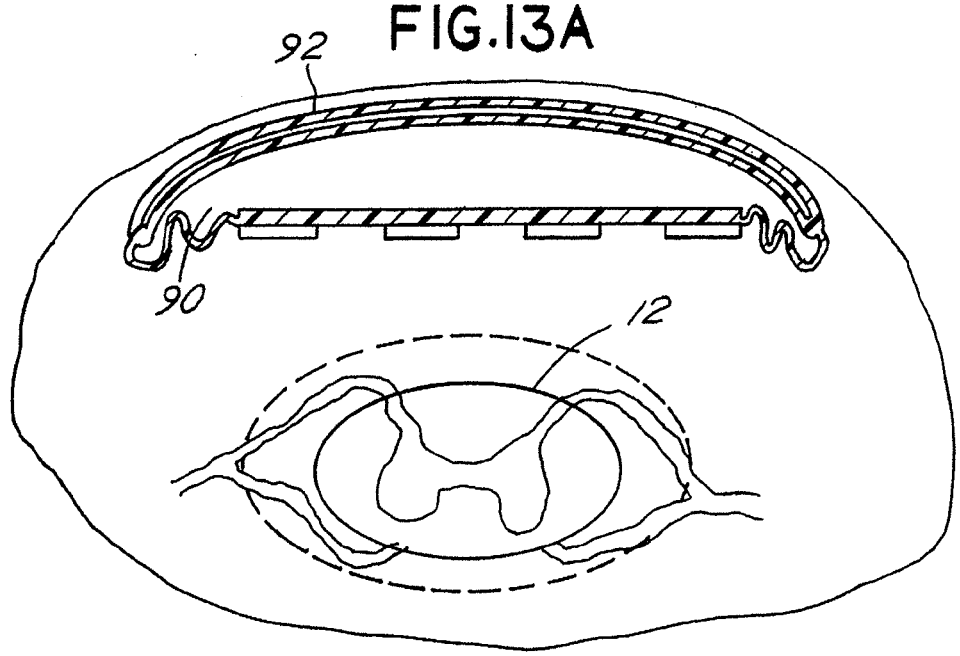
FIGS. 13A-B illustrate another embodiment wherein the balloon includes a rigid or semirigid dorsal component.
Figure 13B:
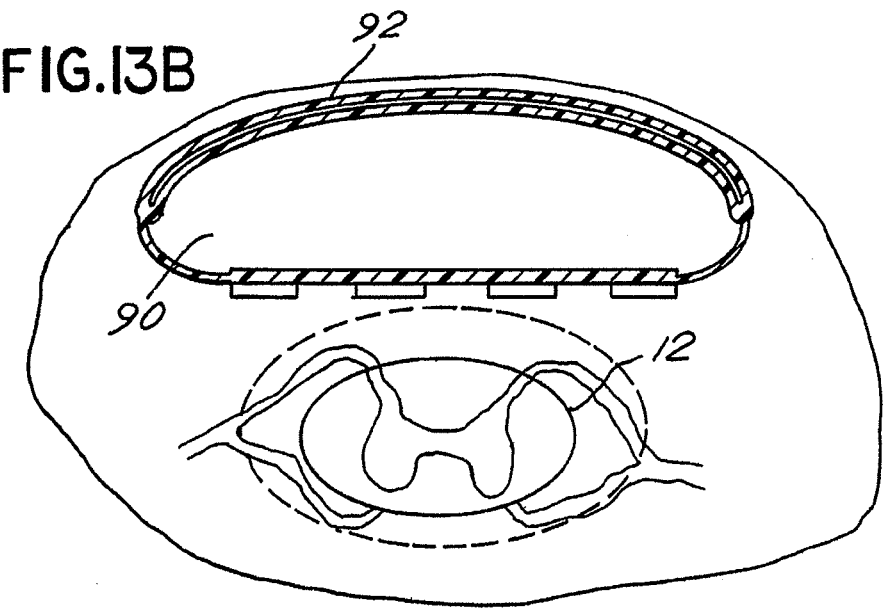
Figure 14A:
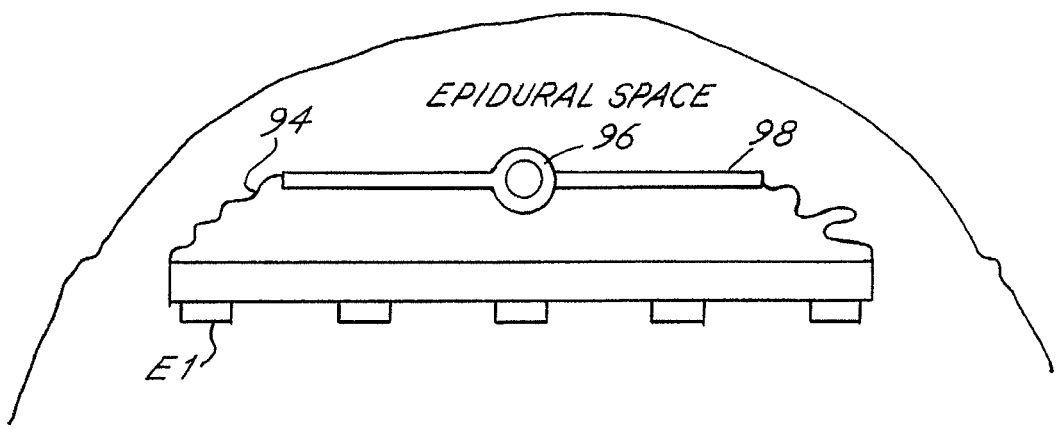
FIGS. 14A-B illustrate yet another embodiment wherein the balloon includes a rigid or semi-rigid dorsal component having a hinge.
Figure 14B:
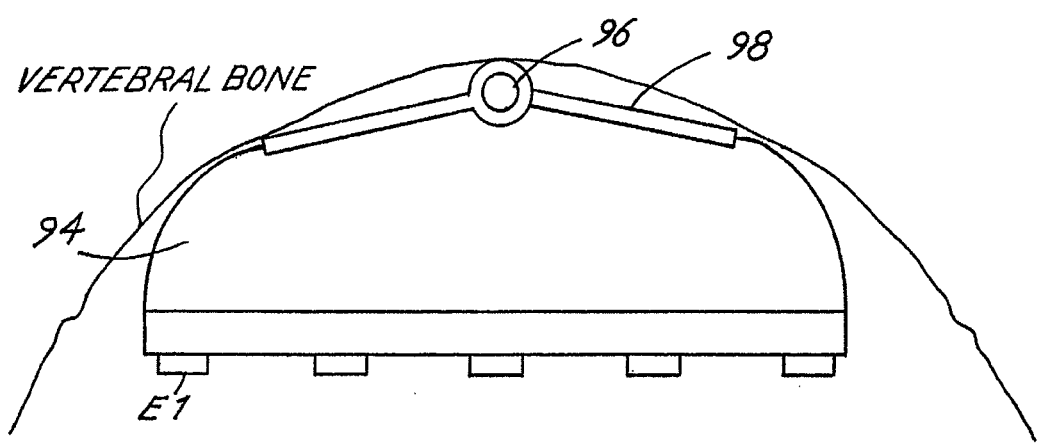

In addition to minimizing lead migration, the present invention also allows the lead to be positioned to be optimally closer to the desired treatment area. The embodiments discussed herein illustrate the various techniques that may be used to non-invasively position and re-position therapy delivery elements after they have been surgically implanted. Positioning of the treatment delivery elements may be laterally in any direction or toward or away from the desired treatment site. FIG. 10 discloses an embodiment of the present invention where a balloon-like structure 60 is implemented on a dorsal side of a paddle lead 62. The balloon may also be positioned on a lateral side of paddle lead 62. Paddle lead 62 may have one or more electrodes 64. Lead 62 may be positioned closer to spinal cord 12 by filling of balloon 60 with a fluid. In the event that it is desired that lead 62 be moved away from spinal cord 12, fluid may be removed from 60. FIGS. 12A-B depict other embodiments wherein a plurality of balloons are implemented to allow more selective adjustment of the electrodes 64 relative to the spinal cord 12. These or other balloons may also be positioned on the sides of the lead so that the lead may be positioned from right to left. FIGS. 13A-B illustrate another embodiment wherein balloon 90 includes a rigid or semi-rigid dorsal component 92. FIGS. 14A-B illustrate yet another embodiment wherein balloon 94 includes a rigid or semirigid dorsal component 98 having a hinge 96 to allow component to form to the shape of the dorsal aspect of the patient's vertebral canal when balloon 94 is filled with fluid.

Figure 11:
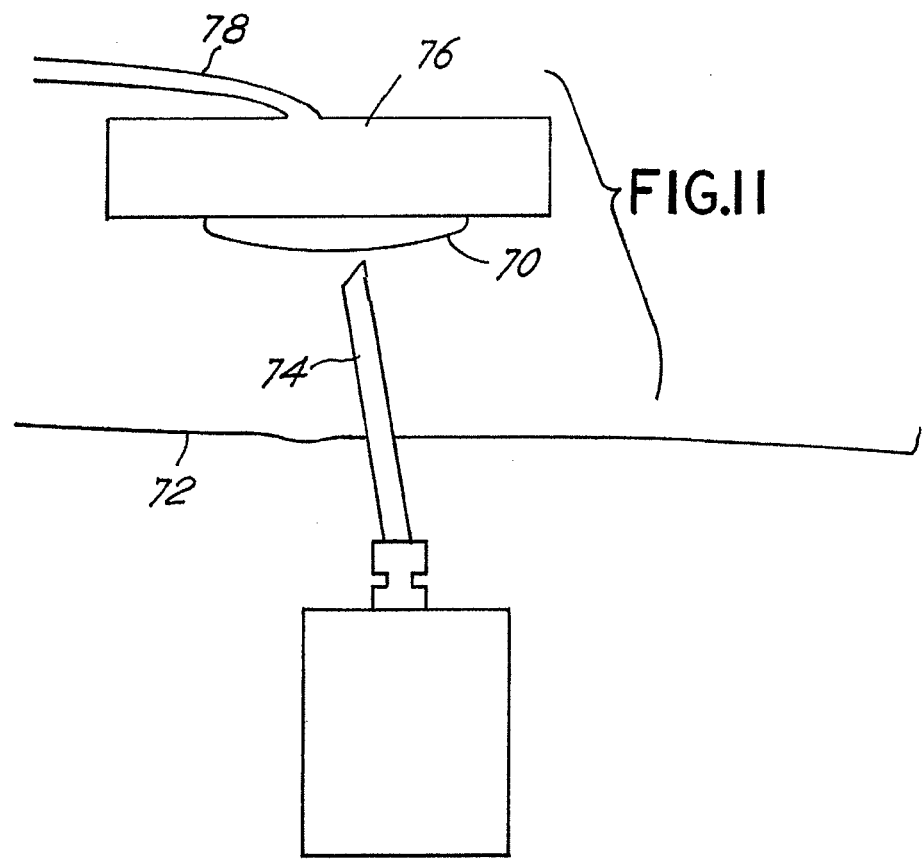
FIG. 11 illustrates an alternative technique for adding or removing fluid to a balloon.
Figure 15:
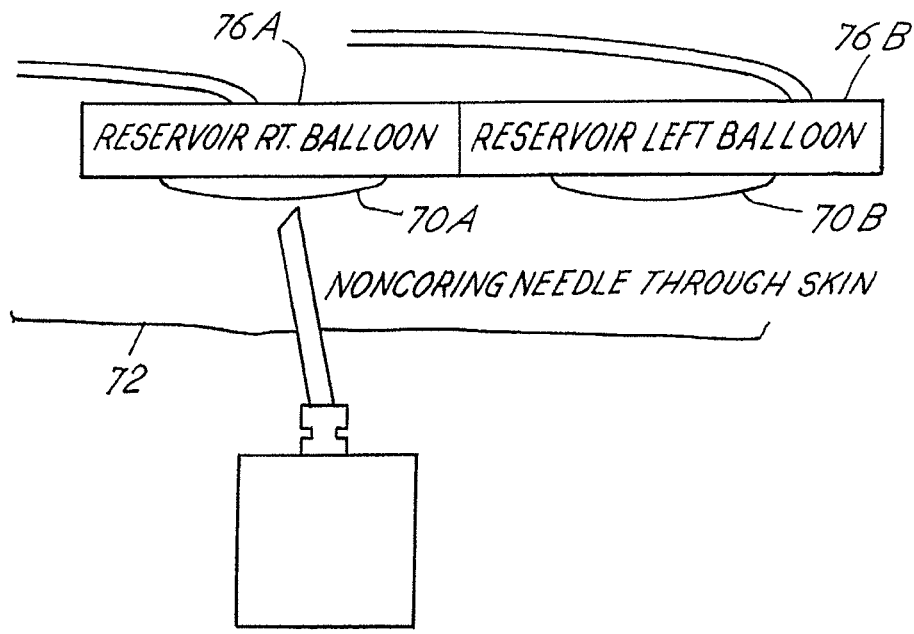
FIG. 15 depicts another embodiment of a reservoir system for adjusting fluid amounts in a lead.
Figure 16:
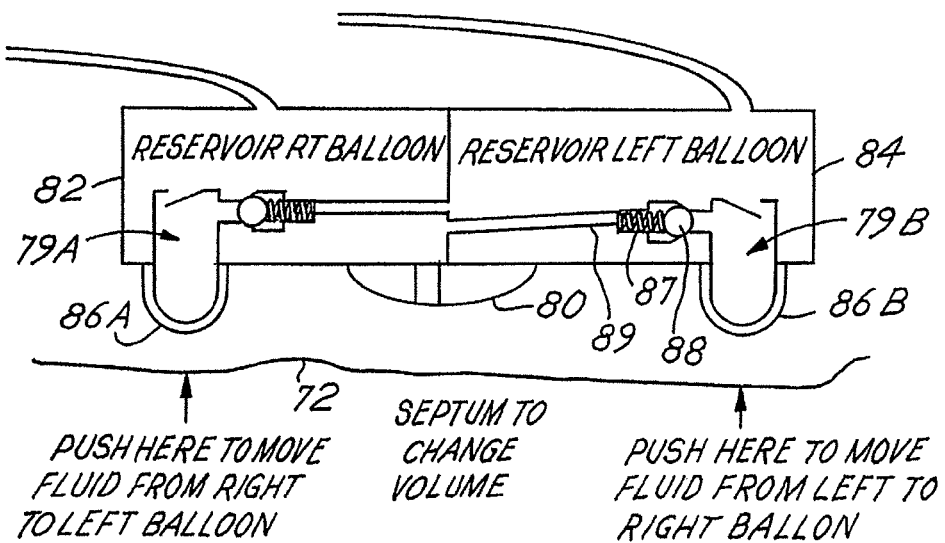
FIG. 16 depicts yet another embodiment a reservoir system for adjusting fluid amounts in a lead.

The amount of fluid in the balloon of FIGS. 12A-B, 13A-B and 14A-B may be controlled by a device similar to the position mechanism of FIG. 2. These balloons may be made of an elastic or inelastic material. FIG. 11 illustrates an alternative technique for adding or removing fluid to balloon 60. A septum 70 is provided just underneath the skin 72 of the patient. A noncoring needle 74 may be utilized to deliver or remove additional fluid to a reservoir 76 via septum 70. The delivery or removal of fluid may then be controlled to any one of the balloons via tube 78 as needed. FIG. 15 depicts another embodiment wherein a separate reservoir and septum pair (reservoir 76A and septum 70A, and reservoir 76B and septum 70B) is provided for each of two balloons. In the case of three balloons, three reservoir/septum pairs may be provided. FIG. 16 discloses yet another embodiment wherein a single septum 80 is provided but reservoirs 82 and 84 may transfer fluid between each other. Each reservoir has an associated bulb or depression mechanism 86A-B that can be accessed externally by pressing on the skin 72 of the patient. Each depression mechanism includes a spring 87 and ball 88 assembly. For example, by depressing mechanism 86B, fluid may be delivered from area 79B of reservoir 84 to reservoir 82 via tube 89. Also, when bulb 86A is depressed, fluid in area 79A is delivered from reservoir 82 to reservoir 84. Also, a separate reservoir may be utilized to add or remove fluid from reservoirs 82 and 84. Such systems are known in the art for an inflatable urinary sphincter and an inflatable penile erector. The system may allow the patient to make these adjustments as needed.

Figure 17A:
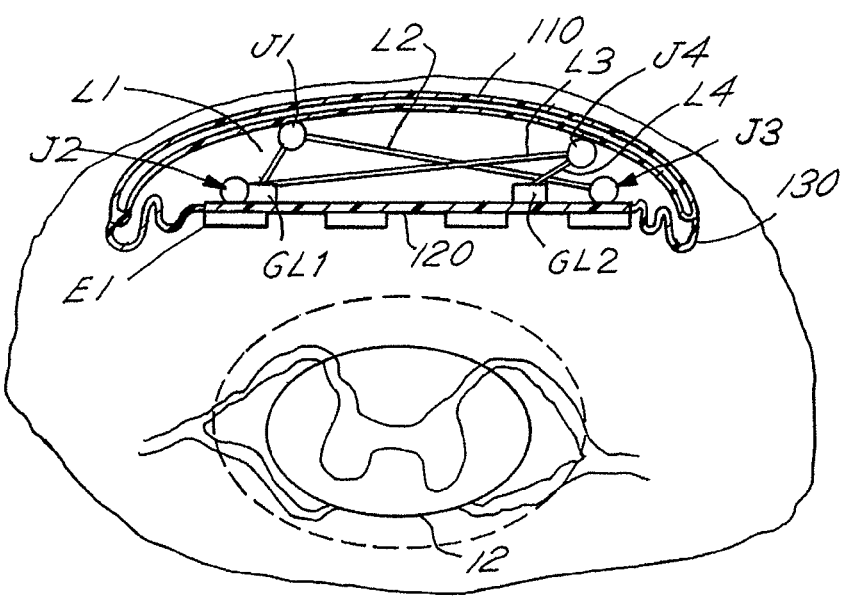
Figure 17B:
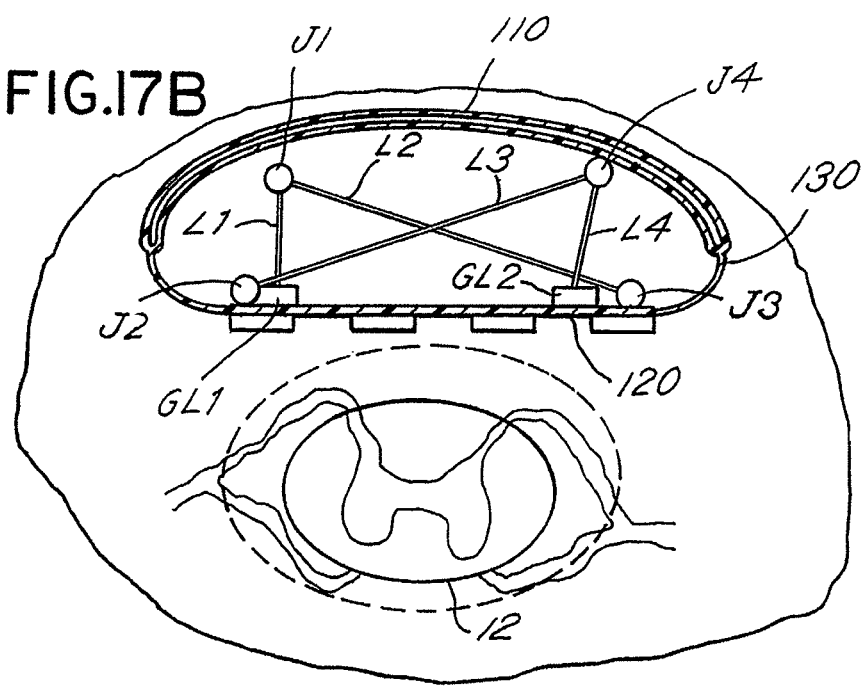
Figure 17C:
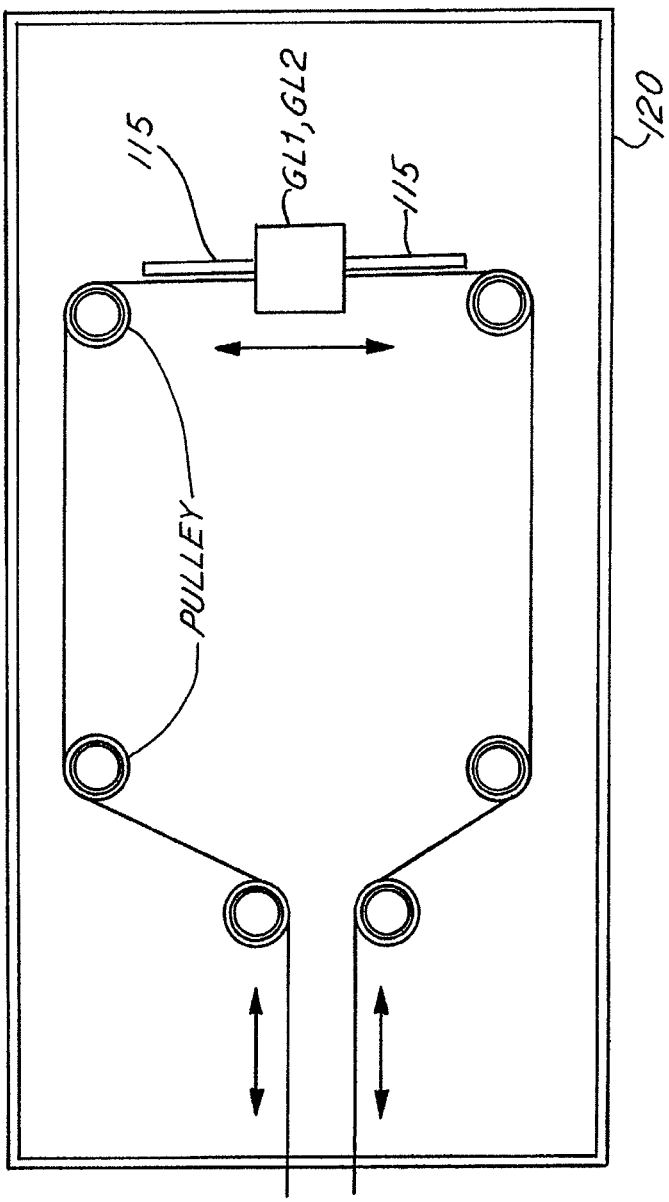

FIGS. 17A-D disclose other embodiments whereby the electrodes are adjusted using gliders GL1 and GL2. As shown in FIGS. 17A-B, gliders GL1 and GL2 are constrained to move along a groove 115 transverse to ventral component 120 of a lead as shown in FIG. 17C. One or more pulley systems with wires may be utilized to move gliders GL1 and GL2 individually or collectively. Referring back to FIGS. 17A-B, gliders GL1 and GL2 are attached to ends of rigid arms L1 and L4 respectively. The opposite ends of arms L1 and L4 are attached to joints J1 and J4 respectively which are fixed relative to a semi-rigid or flexible dorsal component 110. Joints J1 and J4 are also connected to ends of rigid arms L2 and L3 respectively. Opposite ends of arms L2 and L3 are attached to joints J2 and J3 respectively which are fixed relative to ventral component 120 of the lead. The entire assembly may be encased within a membrane-like housing 130 to prevent connective tissue in-growth. Ventral component 120 may be positioned closer to spinal cord 12 by moving glider GL1 and GL2 relative to groove 115. As shown in FIG. 17B, ventral component 120 may be closest to spinal cord when gliders GL1 and GL2 are positioned under the joints J1 and J4. A glider may also be positioned to move parallel to spinal cord 12 along the lead. As shown in FIG. 17D-E, any number of glider geometries may be utilized to adjust the position of ventral component 120.

Figure 18A:
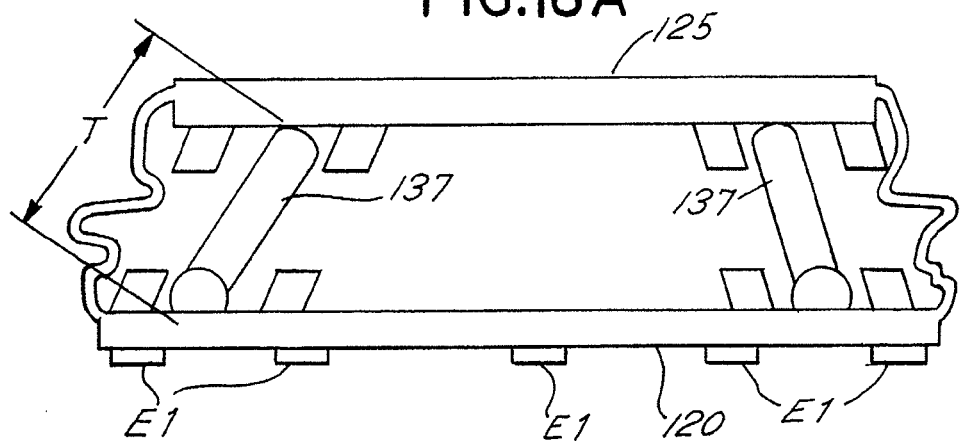
FIGS. 18A-C disclose yet other embodiments whereby a portion of the lead body thickness is adjusted using movable wires.
Figure 18B:
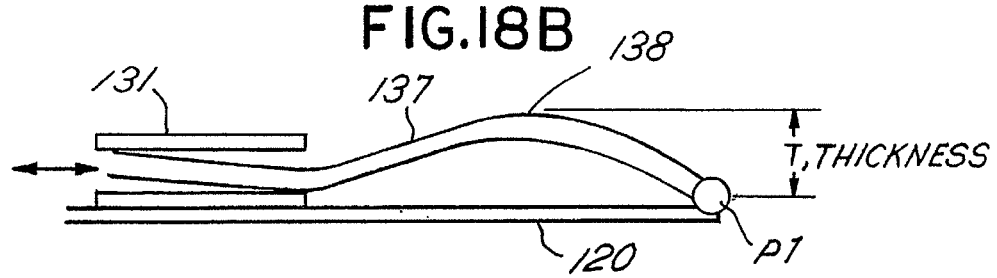
Figure 18C:
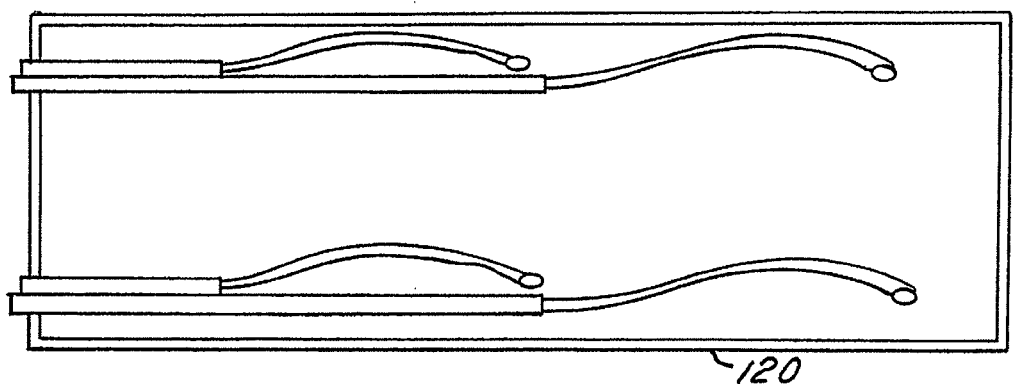

FIGS. 18A-C discloses yet other embodiments whereby the electrodes are adjusted using movable, flexing wires. As shown in FIG. 18A, ventral component 120 of a lead is positioned relative a semi-rigid dorsal component 125. Wires 137 are positioned at opposite sides of the assembly. As shown in FIG. 18B, wire 137 is implemented within a sheath 131 whose end is fixed to ventral component 120. The distal end of wire 137 is anchored at point P1 and is also fixed relative to ventral component 120 of the lead. Wire 137 may be pushed or pulled along sheath 131 causing it to bend or straighten along its body 138. As wire 137 is pushed toward point P1, it bends causing the body 138 to exert pressure against dorsal component 125 and end P1 to exert pressure against ventral component 120. Wire 137 thus causes a portion of ventral component 120 to move away from dorsal component 125 thereby causing a portion of the lead to expand and position electrodes E1 on that portion to move closer to the spinal cord 12. When wire 137 is pulled back away from point P1, wire 137 reduces its pressure exerted on dorsal and ventral components 120 and 125, thereby allowing a portion of the lead to reduce its thickness and electrodes E1 on that portion to move away from spinal cord 12. As shown in FIG. 18C, a plurality of wire assemblies may be incorporated to adjust the position of lead 120 relative to the spinal cord 12 along various points.

Figure 19:
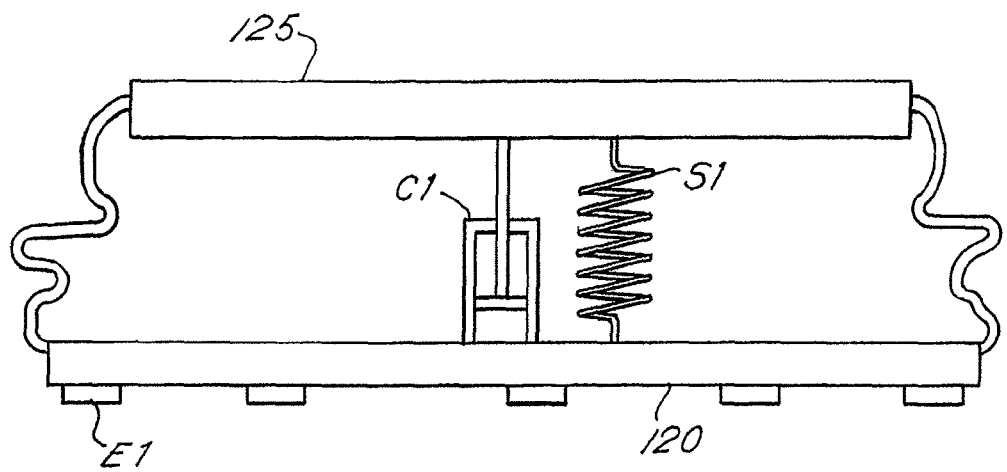
FIG. 19 discloses yet another embodiments whereby a portion of the lead body thickness is adjusted using a piston and a spring.

FIG. 19 discloses yet another embodiment whereby the electrodes are adjusted using a piston C1 and a spring S1. Piston C1 may be moved to push or pull ventral component 120 relative to semi-rigid dorsal component 125. Spring 51 has a preset tension to return ventral component 120 to a default position once the pressure exerted by piston C1 is removed. As in the previously discussed embodiments, more than one piston/spring assembly may be located laterally as well as along the length of lead. Alternatively, bellows may be used in place of piston C1 and spring S1.

Figure 20:
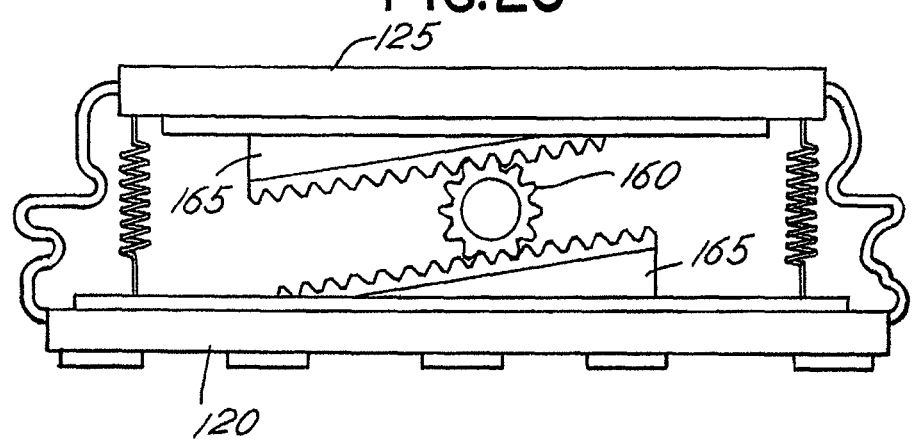
FIG. 20 discloses yet another embodiment whereby a portion of the lead body thickness is adjusted using a gear mechanism.

FIG. 20 discloses yet another embodiment whereby the lead is adjusted using a gear mechanism. A gear 160 may be rotated about an axis but is held in a fixed position relative to either semi-rigid dorsal component 125 or ventral component 120. Slidable elements 165 have ramped surfaces with teeth that interact with gear 160. The upper element 165 is coupled to slide relative to semi-rigid dorsal component 125 and the lower slidable element is coupled to slide relative to ventral component 120. As gear rotates, slidable elements 165 are moved in opposite directions relative to each other. With a clockwise turn of gear 160, lower element 165 slides to the left and upper element slides to the right. The elements thereby push ventral component 120 away from semi-rigid dorsal component 125 and toward spinal cord 12. Two or more gears may be implemented to minimize asymmetry in lead thickness.

Figure 21A:
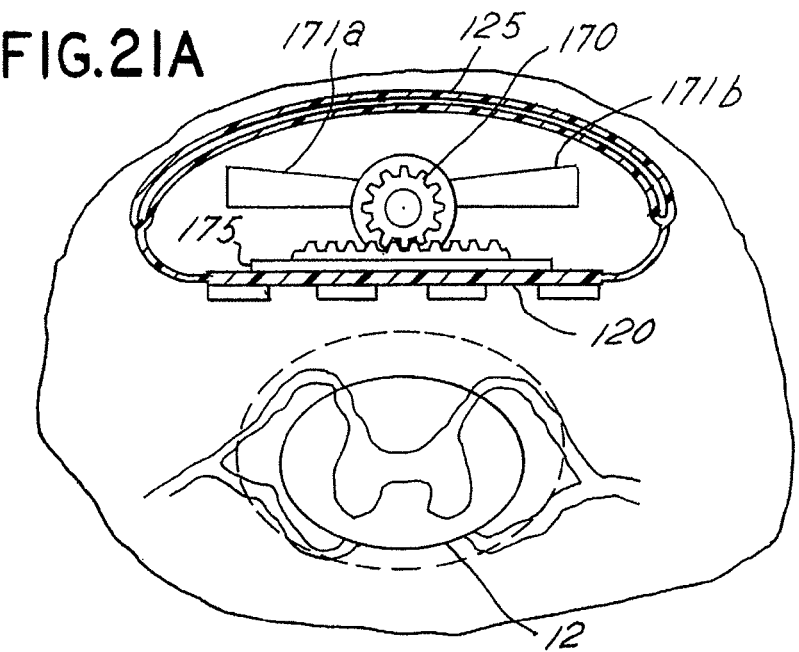
FIGS. 21A-C disclose various embodiments of the present invention utilizing a single or dual gear mechanism.
Figure 21B:
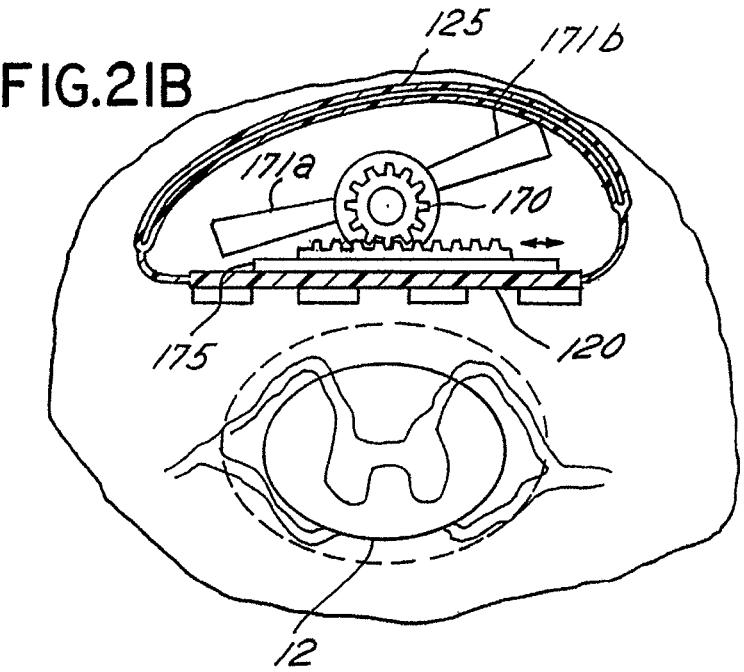
Figure 21C:
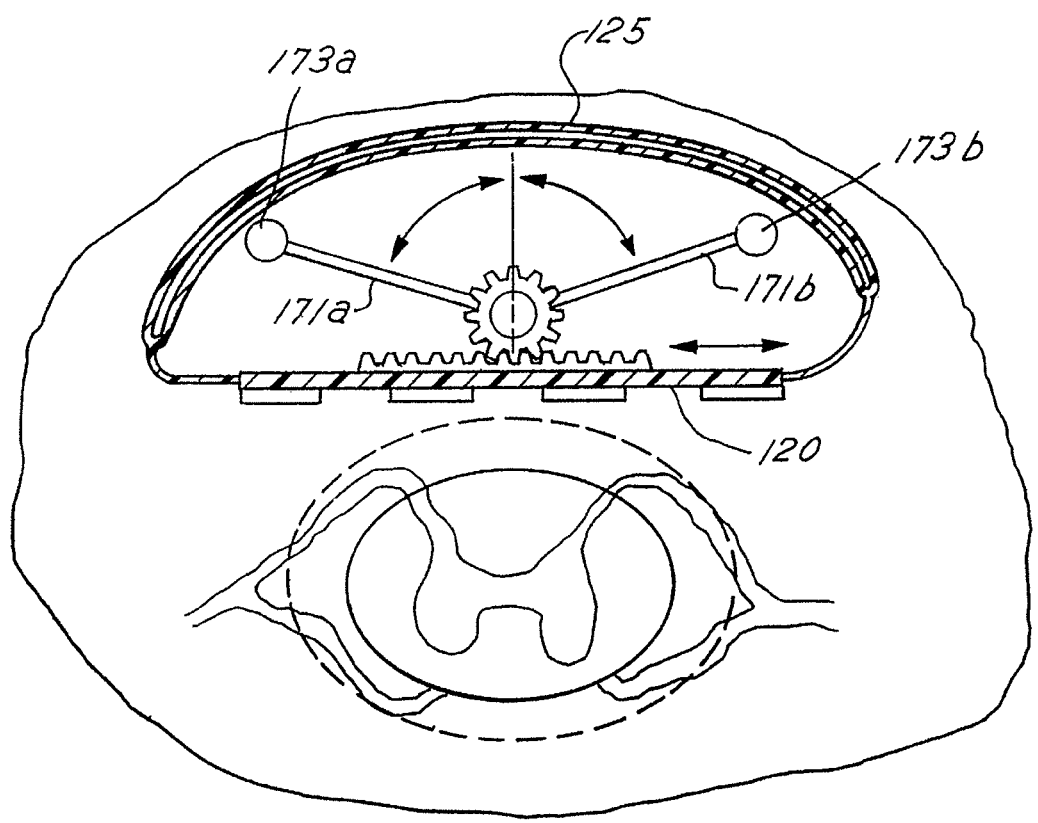

As shown in FIGS. 21A-C, a gear mechanism may be incorporated into any number of embodiments. FIG. 21A discloses a toggle mechanism having one gear 170 attached to a component with an associated left or right wing 171a or 171b. As gear 170 is rotated, wings 171a-b are rotated accordingly. As shown in FIG. 21B, rotation of wings 171a-b counter-clockwise pushes up against semi-rigid dorsal component 125 causing that portion of lead to increase its thickness, thereby moving that portion of ventral component 120 toward spinal cord 12. Gear 170 may be controlled by slidable toothed elements 175. As shown in FIG. 21C, there may be two gears (one is shown), each connected to a single-sided wing 171*a* or 171*b* to change the lateral lead thickness independently. Wings 171*a-b* may also have transverse extensions 173*a-b* (parallel to spinal cord 12) to push against dorsal component 125.

The lead may be configured in any number of ways using any combination of the above-detailed structures. For example, FIGS. 22 and 23 illustrate that two or more of the above-detailed techniques (such as wings, flexing wires and/or springs) may be combined to provide the desired control of lead thickness.

FIG. 24 illustrates yet another embodiment of a lead according to a preferred embodiment of the present invention for use in SCS therapy. This design allows movement of electrodes toward or along spinal nerve roots within the spinal canal as they pass caudally and laterally toward their respective foraminae (exits from the vertebral bones). In accordance with known techniques, a Tuohy needle 314 is utilized and positioned near the spinal cord. Lead body 318 is inserted through the lumen 316 of Tuohy needle 314 and positioned near the spinal cord 12. A proximal end (not shown) of lead body 318 is ultimately to be connected to a source device (not shown) which may be signal generator 14 of FIG. 1, in the case of electrical stimulation, or a drug pump in the case of drug therapy. Lead 318 is provided with a distal tip 320 that may be compacted for insertion and unfolded after it has been positioned appropriately within the body. Distal tip 320 includes a central portion 322 and at least one span 324 depending therefrom. Span 324 is comprised of a flexible, insulative material, such as polyurethane or silicone rubber. The term "flexible" as used herein refers to both resilient and non-resilient materials. Central portion 322 may have a generally semi-circular cross-section as shown, or may be flat such as in the case of a paddle lead (exemplified in FIG. 26). Affixed to a surface of spans 324 and to central portion 322 is a series of electrodes 326. In accordance with the invention, lead 320 may be configured into a compact insertion position for ease of insertion through lumen 316 of Tuohy needle 314.

Once in position near the implant site, lead tip 320 may be deployed out of Tuohy needle 314, as shown in FIG. 24. In the embodiment of FIG. 24, spans 324 are semirigid and tend to span out at a predetermined angle. To optimally position lead spans 324 along spinal nerve roots, lead 320 may be pulled back into the Tuohy needle 314. As it moves back, spans 324 will tend to move laterally as well as downward, along the path of a nerve root. Needle 314 may be replaced by a sheath component for adjustments after implant. In the embodiment of FIG. 25, spans 324 may be rigid or flaccid and are coupled to a lever 330 capable of adjusting the lateral displacement of spans 324. Lever 330 extends from spans 324 to body struts 319. Struts 319 pass inside or along lead body 318 to controllers (not shown). As lever 330 is moved toward distal end of lead 320 by pushing on struts 319, spans 324 are displaced further in a lateral direction. Lever 330 may be coupled to a control mechanism such that spans 324 may be re-positioned at future times to provide optimal treatment therapy. FIG. 26, discloses another embodiment of a paddle lead 419 having spans 418 which can rotate to lateral positions. FIGS. 27A-B disclose yet another embodiment of a paddle lead 520 capable of extending electrodes laterally to track along spinal nerves. Such a mechanism may be similar to that of a car antenna-like device whereby a rigid or semi-rigid wire may extend laterally from lead 520. An internal stylet 521 may be utilized to adjust the length of the span 522. As shown in FIG. 27A, when stylet 521 is inserted within the lead 520 and is closest to the lead tip, the span 522 is retracted and inside lead 520. As stylet 521 is pulled to the left, span 522 is directed out as shown in FIG. 27B to direct electrodes 523 laterally away from lead 520. This embodiment may be incorporated with the embodiments of FIGS. 24-26 and 27A-B to allow adjustment of the extent of the lateral displacement as well as the angle of the lateral displacement.

The above embodiments illustrate various techniques for allowing therapy delivery elements to be positioned during and/or after implant to effectively provide treatment therapy to the targeted area of the spinal cord or brain. Further, relief may be provided with a lower amplitude, and motor or other undesirable side effects may be minimized. As exemplified in the above embodiments, any number of techniques may be utilized.

The present invention may also be utilized within the brain to provide electrical stimulation as well as delivery of one or more drugs. The present invention may be implemented within a system as disclosed in U.S. patent application Ser. No. 09/302,519 entitled "Techniques For Selective Activation Of Neurons In The Brain, Spinal Cord Parenchyma[, and] or Peripheral Nerve," invented by Mark Rise and Michael Baudino, now U.S. Pat. No. 6,353,762, which is incorporated herein by reference in its entirety. Treatment therapy may be provided to the brain to treat any number of diseases. Sometimes, the disease will progress to another part of the brain. The present invention may thereby be used to advance the electrodes to a different part of the brain. For example, electrodes and/or catheters may be implanted within the brain to treat tremor. Later, it may be desirable to address symptoms of akinesia or bradykinesia which were not clearly present when the treatment device was originally implanted. The present invention may thereby extend or shorten the leads to effect different areas of the brain tissue. Alternatively, leads may be adjusted to achieve optimal positioning.

Figure 37A:
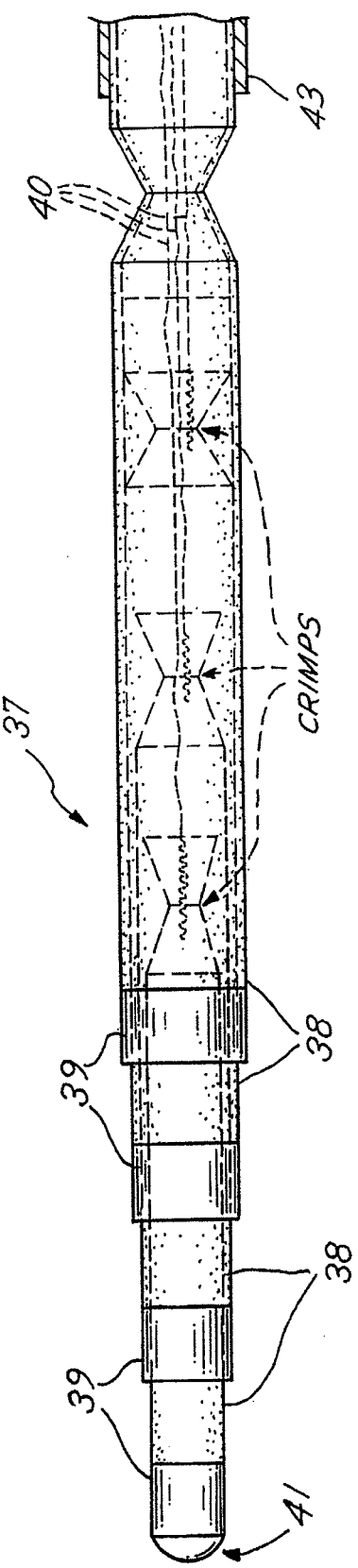
FIGS. 37A-B illustrate an embodiment of an extendable lead for implant within a brain.
Figure 37B:
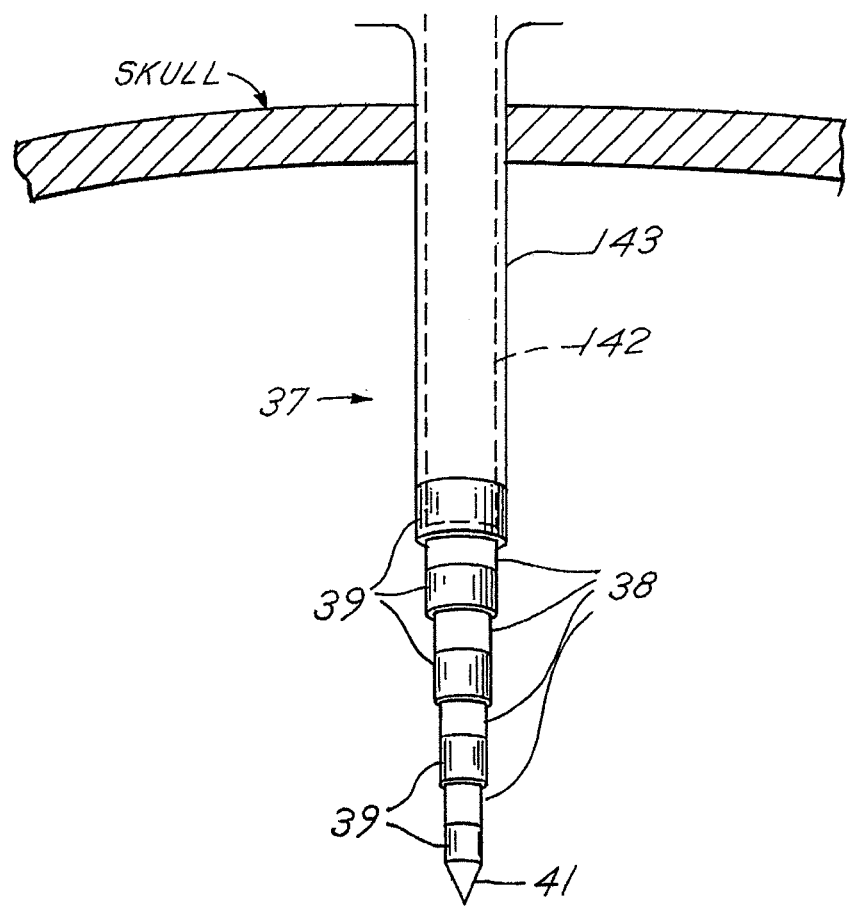

For example FIG. 37A depicts a lead 37 composed of concentric tubes 38, preferably metal such as platinum. These tubes may be coated with a polymer except for the distal end portions 39 that serve as the electrodes. The conductive wires 40 carrying energy to the electrodes are in the interior of the concentric tubes. Optionally, the most distal electrode end 41 may be a small recording microelectrode to help assist in the actual placement of the lead. As shown in FIG. 37B, the lead 37 may be implanted within the brain under known techniques. A pusher 142 may be placed into the lead through the proximal portion to make the lead 37 stiff during the introduction phase and/or to provide a mechanism to push the concentric tubes 38 out and away from the outer tube or cannula 143. After implant, the outer cannula 143 may optionally be removed.

The present invention may be operated as an open-loop controlled system. In an open-loop system, the physician or patient may at any time manually or by the use of pumps or motorized elements adjust the positioning of the electrodes in situ and change stimulation parameters. However, this subsequent position adjustment would be independent of any intended changes in stimulation effect or side-effects the patient may be experiencing, and an iterative procedure may be necessary.

Optionally, the present invention may incorporate a closed-loop control system which may automatically adjust (1) the positioning of the electrodes in response to a sensed condition of the body such as a response to the treatment therapy; and/or (2) the electrical stimulation parameters in response to a sensed symptom or an important related symptom indicative of the extent of the disorder being treated. Under a closed-loop feedback system to provide automatic adjustment of the positioning of the electrodes, a sensor 130A (FIG. 28) that senses a condition of the body is preferably utilized. For example, sensor 130A may detect patient position to discern whether the patient is lying down or is in an erect position. Typically, spinal cord stimulation becomes strong when the patient lies down due to the spinal cord moving in a dorsal direction toward the lead. In such a situation, the position control mechanism may adjust electrodes to move away from spinal cord. Alternatively, one or more recording electrodes may be utilized to provide feedback.

More detailed description of sensor 130A, other examples of sensors and the feedback control techniques are disclosed in U.S. Pat. No. 5,716,377 entitled "Method of Treating Movement Disorders By Brain Infusion," issued on Feb. 10, 1998 and assigned to Medtronic, Inc., which is incorporated herein by reference in its entirety.

Figure 28:
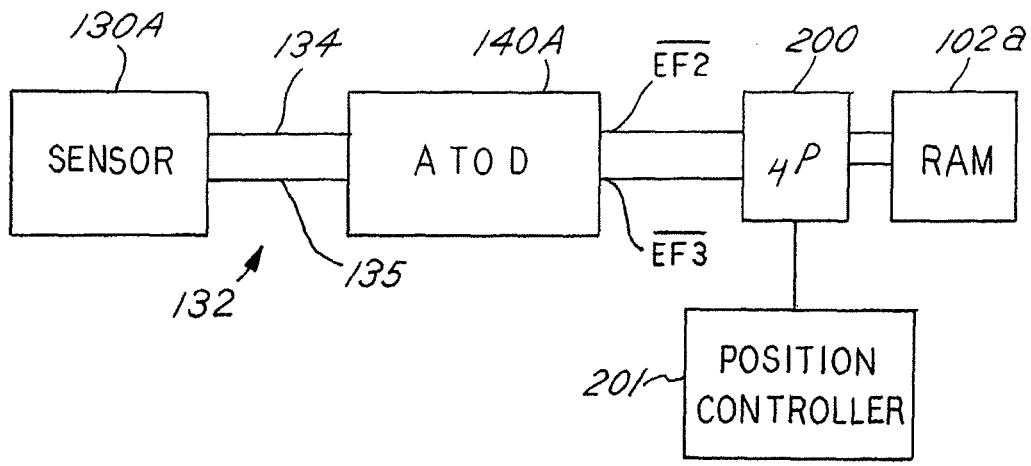
FIG. 28 is a schematic block diagram of a sensor and an analog to digital converter circuit used in a preferred embodiment of the invention.
Figure 29:
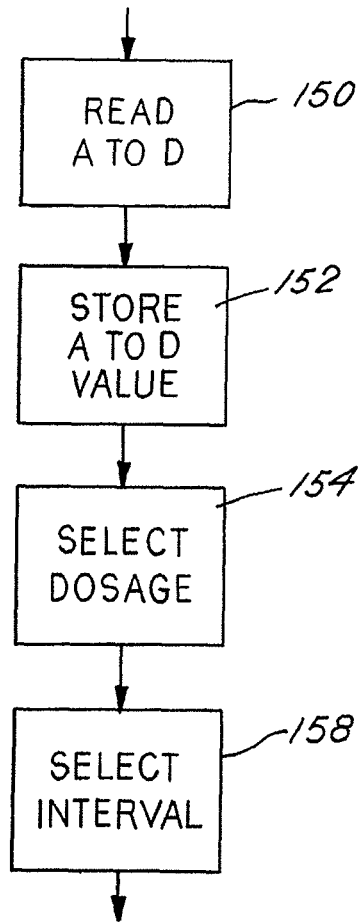
FIG. 29 is a flow chart illustrating a preferred form of a microprocessor program for utilizing the sensor to control the treatment therapy provided to the neural tissue.

Referring to FIG. 28, the output of sensor 130A is coupled by a cable 132 comprising conductors 134 and 135 to the input of analog to digital converter 140A. Alternatively the output of the sensor 130A could communicate through a "body bus" communication system as described in U.S. Pat. No. 5,113,859 (Funke), assigned to Medtronic which is incorporated by reference in its entirety. Alternatively, the output of an external feedback sensor 130A would communicate with signal generator 14 through a telemetry down-link. The output of the analog to digital converter 140A is connected to a microprocessor 200 via terminals EF2 BAR and EF3 BAR. The sensor signals may then be stored in a memory device such as a Random Access Memory (RAM) 102a. Such a configuration may be one similar to that shown in U.S. Pat. No. 4,692,147 ("'147 patent") except that before converter 140A is connected to the terminals, the demodulator of the '147 patent (identified by 101) would be disconnected. Microprocessor 200 may then be coupled to a position controller 201.

For some types of sensors, microprocessor 200 and analog to digital converter 140A would not be necessary. The output from sensor 130A can be filtered by an appropriate electronic filter in order to provide a control signal for position controller. An example of such a filter is found in U.S. Pat. No. 5,259,387 "Muscle Artifact Filter, Issued to Victor de Pinto on Nov. 9, 1993, incorporated herein by reference in its entirety.

Figure 30:
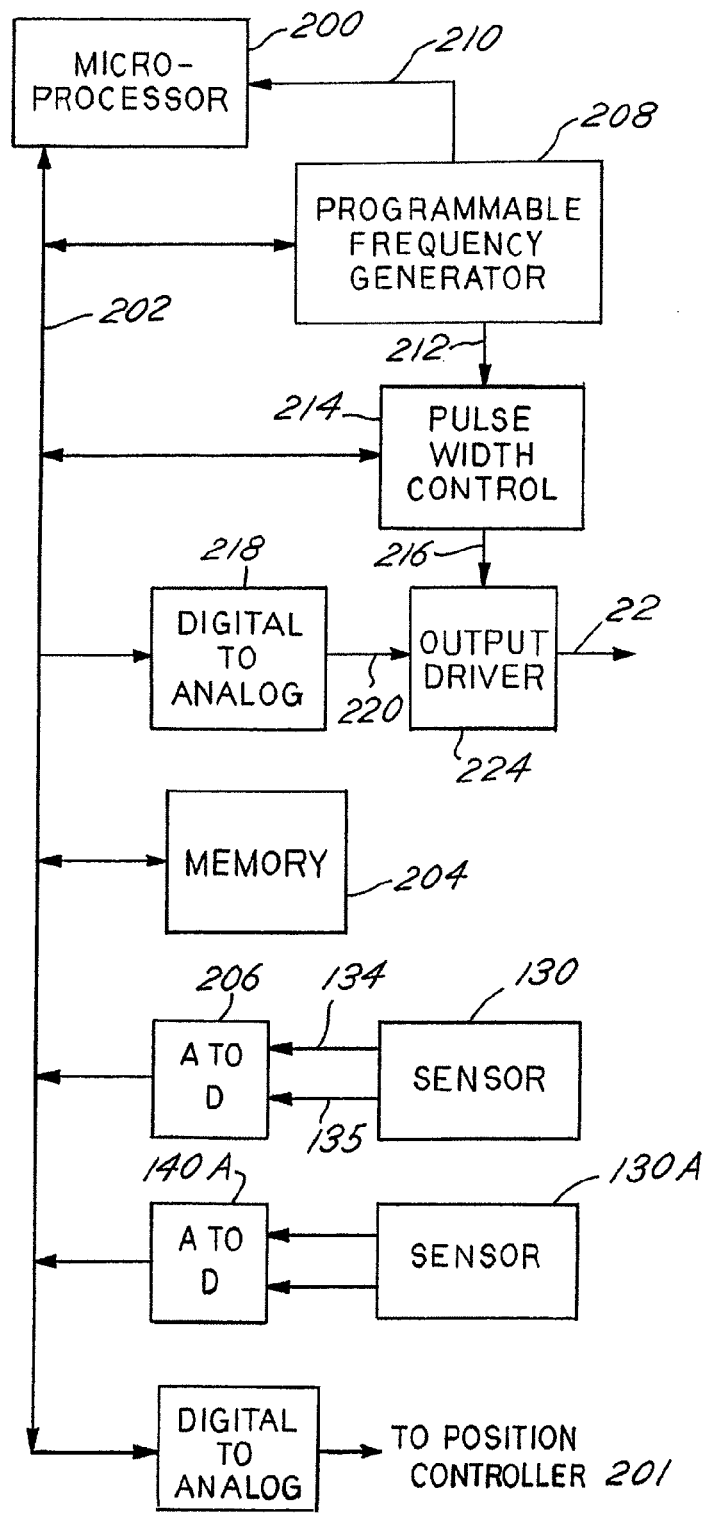
FIG. 30 is a schematic block diagram of a microprocessor and related circuitry used in a preferred embodiment of the invention.

Closed-loop control of position controller can be achieved by a modified form of the ITREL II signal generator. Referring to FIG. 30, the output of the analog to digital converter 140A is connected to microprocessor 200 through a peripheral bus 202 including address, data and control lines. Microprocessor 200 processes the sensor data in different ways depending on the type of transducer in use. Microprocessor may adjust the position of the electrodes in response to the sensor signal information provided by sensor 130A. The type of control provided depends upon the type of position controller utilized and the mechanism utilized (discussed above) to position the electrodes. In the case where position controller relies on electrical energy to cause mechanical movement (e.g., pumps, motors and the like) or is purely electrical control, microprocessor 200 or a second microprocessor may serve as the position controller. In the case where position requires mechanical control, an appropriate controlling device is used. For example, in the embodiment of FIGS. 10-16 where position is controlled by filling a balloon with fluid, position controller may be incorporated within a reservoir system for holding the fluid outside the lead's balloon. Torque from percutaneous instruments that engages in a mechanical component may also be used.

The present invention may also incorporate a closed-loop feedback system to provide automatic adjustment of the electrical stimulation therapy. Such is system is disclosed in U.S. Pat. No. 5,792,186 entitled "Method and Apparatus of Treating Neurodegenerative Disorders by Electrical Brain Stimulation," and assigned to Medtronic, Inc., which is incorporated herein by reference in its entirety. The system may incorporate the same sensor 130A discussed above or one or more additional sensors 130 to provide feedback to provide enhanced results. Sensor 130 can be used with a closed loop feedback system in order to automatically determine the level of electrical stimulation necessary to provide the desired treatment. For example, to treat motion disorders that result in abnormal movement of an arm, sensor 130 may be a motion detector implanted in the arm. More detailed description of sensor 130, other examples of sensors and the feedback control techniques are disclosed in U.S. Pat. No. 5,716,377 entitled "Method of Treating Movement Disorders By Brain Infusion," issued on Feb. 10, 1998 and assigned to Medtronic, Inc., which is incorporated herein by reference in its entirety. Other such sensors are also disclosed in U.S. Pat. Nos. 5,683,422; 5,702,429; 5,713,923; 5,716,316; 5,792,186; 5,814,014; and 5,824,021.

Closed-loop electrical stimulation can be achieved by a modified form of the ITREL II signal generator which is described in FIG. 30. The output of the analog to digital converter 206 is connected to a microprocessor 200 through a peripheral bus 202 including address, data and control lines. Microprocessor 200 processes the sensor data in different ways depending on the type of transducer in use. When the signal on sensor 130 exceeds a level programmed by the clinician and stored in a memory 204, increasing amounts of stimulation will be applied through an output driver 224. For some types of sensors, a microprocessor and analog to digital converter will not be necessary. The output from sensor 130 can be filtered by an appropriate electronic filter in order to provide a control signal for signal generator 14. An example of such a filter is found in U.S. Pat. No. 5,259,387 "Muscle Artifact Filter, Issued to Victor de Pinto on Nov. 9, 1993, incorporated herein by reference in its entirety.

Still referring to FIG. 30, the stimulus pulse frequency is controlled by programming a value to a programmable frequency generator 208 using bus 202. The programmable frequency generator 208 provides an interrupt signal to microprocessor 200 through an interrupt line 210 when each stimulus pulse is to be generated. The frequency generator 208 may be implemented by model CDP1878 sold by Harris Corporation. The amplitude for each stimulus pulse is programmed to a digital to analog converter 218 using bus 202. The analog output is conveyed through a conductor 220 to an output driver circuit 224 to control stimulus amplitude. Microprocessor 200 also programs a pulse width control module 214 using bus 202. The pulse width control 214 provides an enabling pulse of duration equal to the pulse width via a conductor. Pulses with the selected characteristics are then delivered from signal generator 14 to the lead to the target locations of spinal cord 12.

Figure 31:
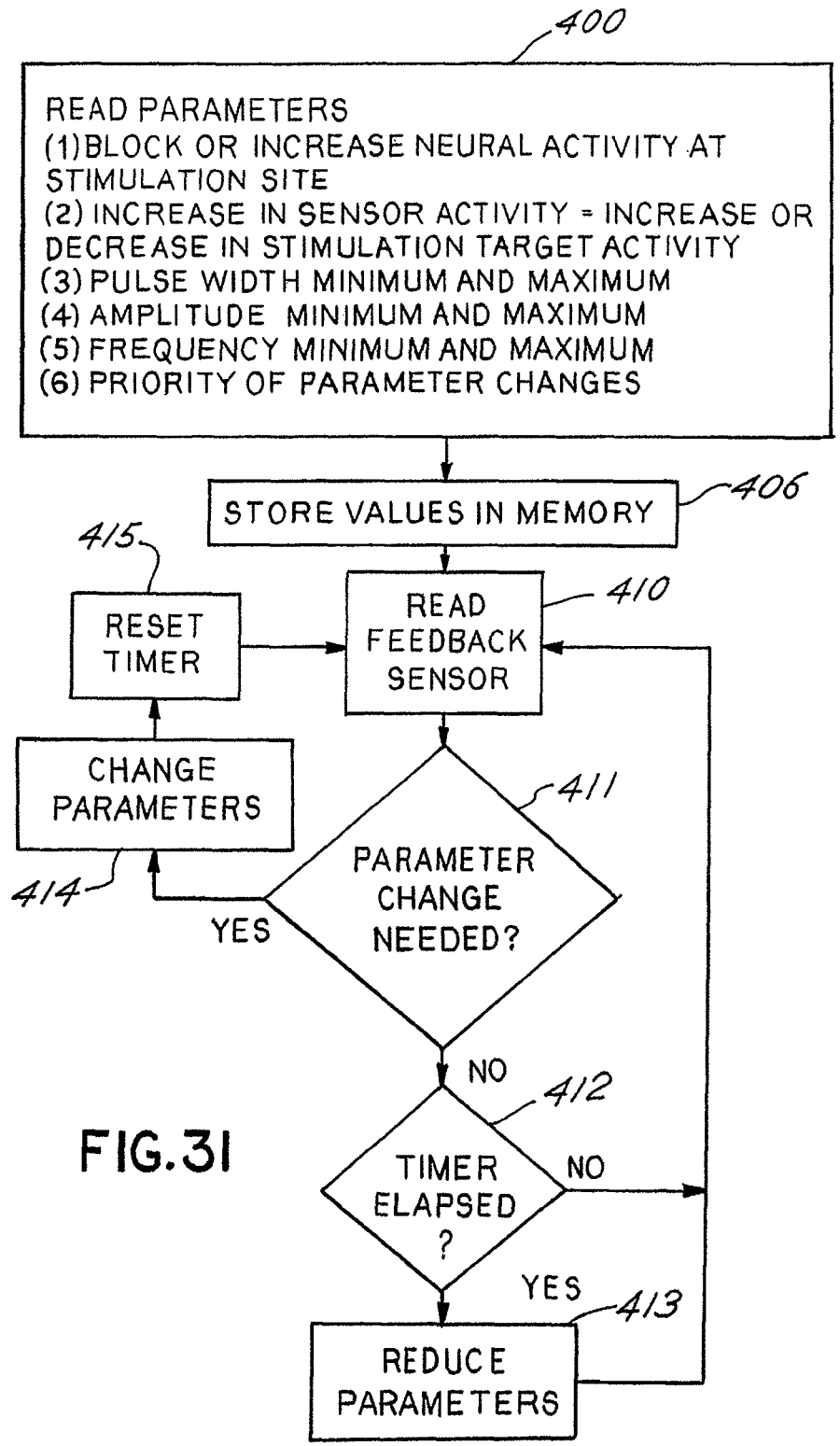
FIGS. 31-35 are flow charts illustrating a preferred form of a microprocessor program for generating stimulation pulses to be administered to neural tissue.

Microprocessor 200 executes an algorithm shown in FIGS. 31-5 to provide stimulation with closed loop feedback control. At the time the stimulation signal generator 14 or an alternative device having stimulation and/or infusion functions is implanted, the clinician programs certain key parameters into the memory of the implanted device via telemetry. These parameters may be updated subsequently as needed. Step 400 in FIG. 31 indicates the process of first choosing whether the neural activity at the stimulation site is to be blocked or facilitated (step 400(1)) and whether the sensor location is one for which an increase in the neural activity at that location is equivalent to an increase in neural activity at the stimulation target or vice versa (step 400(2)). Next the clinician must program the range of values for pulse width (step 400(3)), amplitude (step 400(4)) and frequency (step 400(5)) which signal generator 14 may use to optimize the therapy. The clinician may also choose the order in which the parameter changes are made (step 400(6)). Alternatively, the clinician may elect to use default values.

The algorithm for selecting parameters is different depending on whether the clinician has chosen to block the neural activity at the stimulation target or facilitate the neural activity. FIGS. 31-35 detail the steps of the algorithm to make parameter changes.

Figure 32:
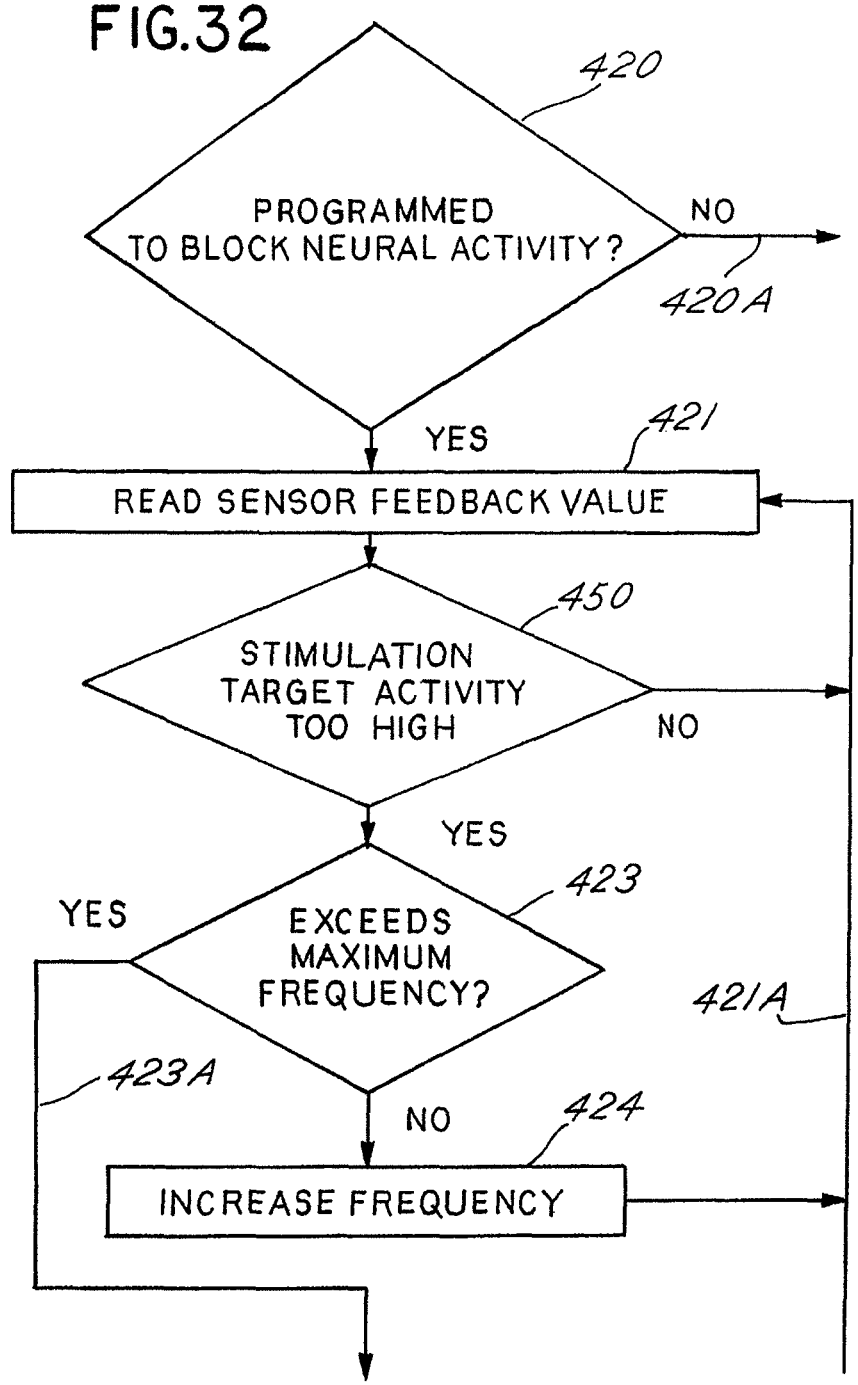
Figure 33:
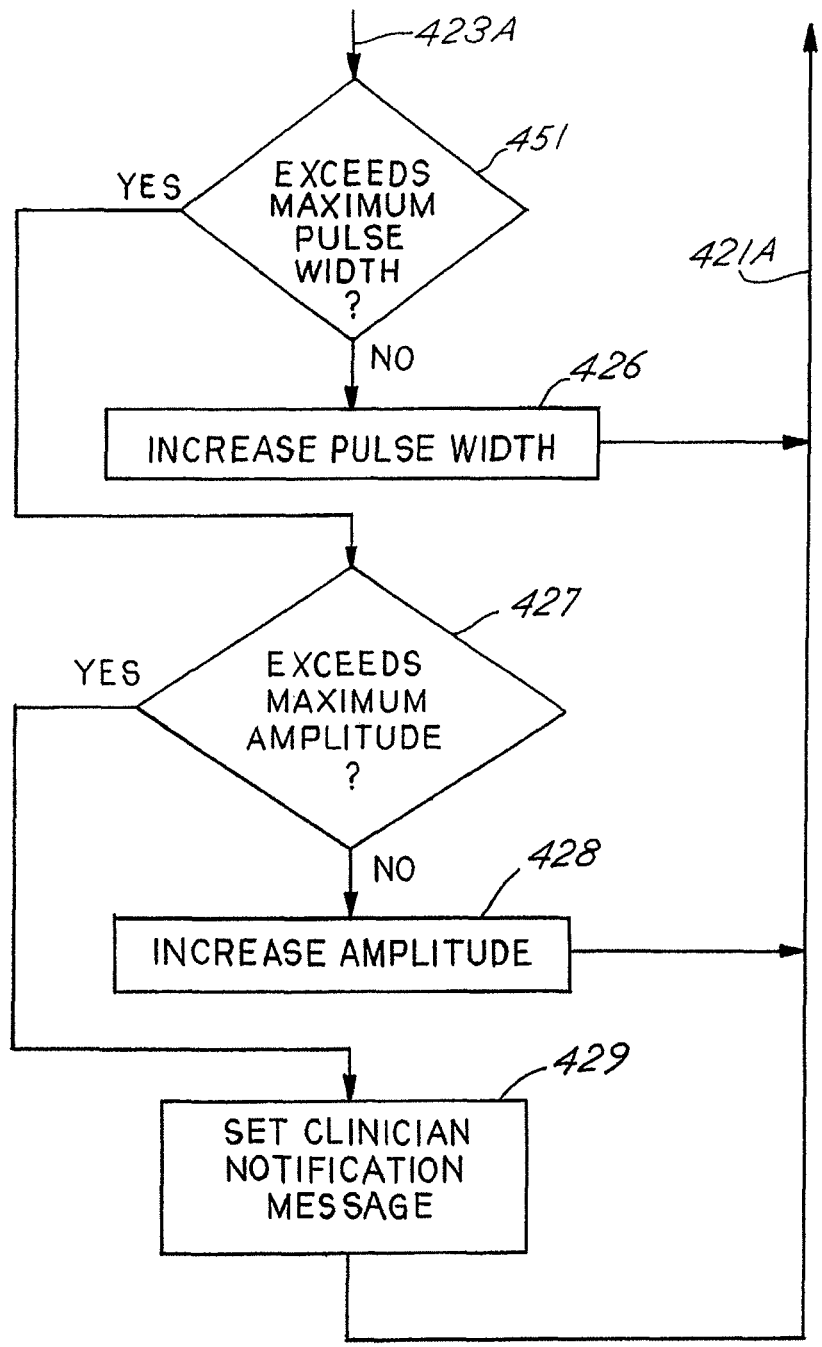
Figure 34:
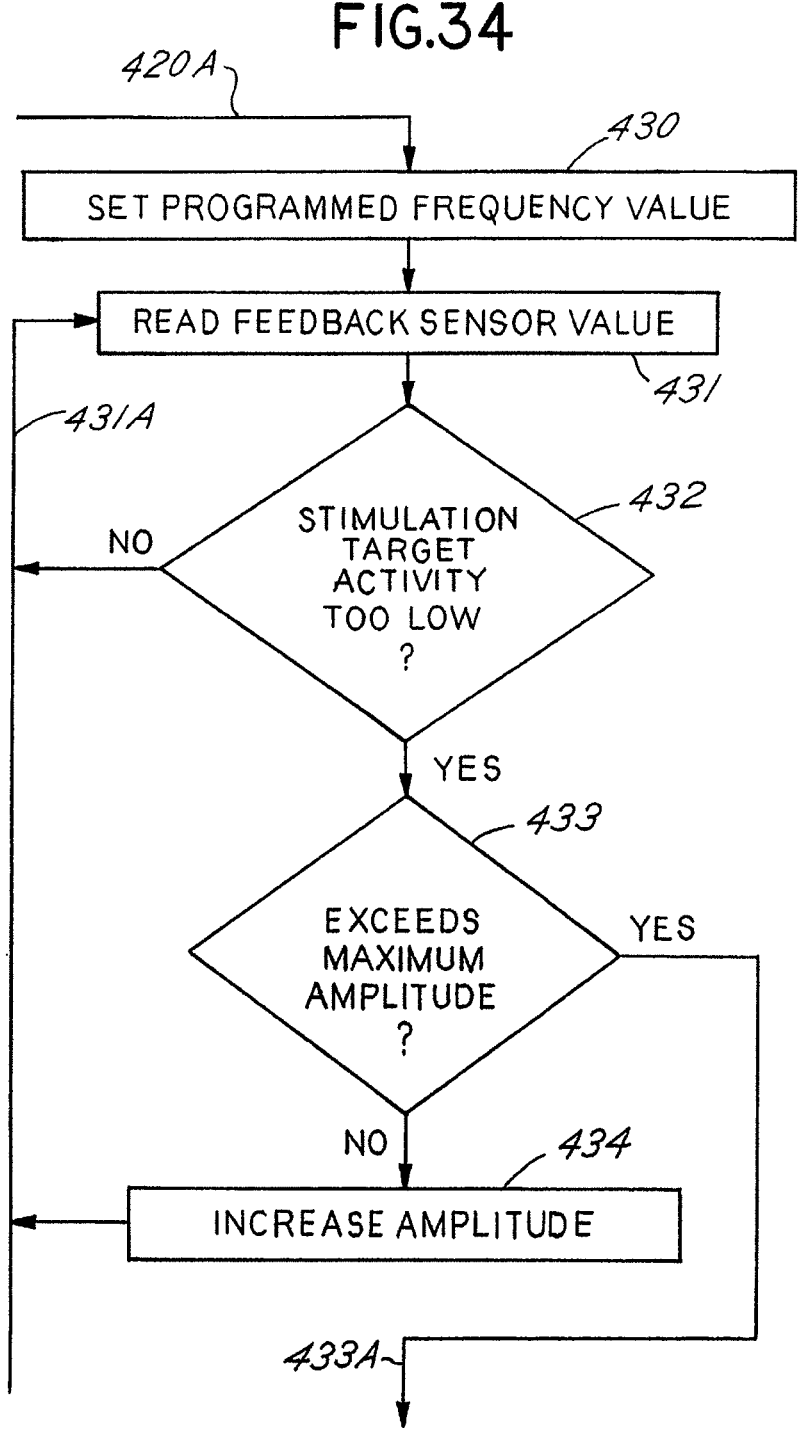

The algorithm uses the clinician programmed indication of whether the neurons at the particular location of the stimulating electrode are to be facilitated or blocked in order to decide which path of the parameter selection algorithm to follow (step 420, FIG. 32). If the neuronal activity is to be blocked, signal generator 14 first reads the feedback sensor 130 in step 421. If the sensor values indicate the activity in the neurons is too high (step 450), the algorithm in this embodiment first increases the frequency of stimulation in step 424 provided this increase does not exceed the preset maximum value set by the physician. Step 423 checks for this condition. If the frequency parameter is not at the maximum, the algorithm returns to step 421 through path 421A to monitor the feed back signal from sensor 130.

If the frequency parameter is at the maximum, the algorithm next increases the pulse width in step 426 (FIG. 33), again with the restriction that this parameter has not exceeded the maximum value as checked for in step 451 through path 423A. Not having reached maximum pulse width, the algorithm returns to step 421 to monitor the feedback signal from sensor 130. Should the maximum pulse width have been reached, the algorithm next increases amplitude in a like manner as shown in steps 427 and 428. In the event that all parameters reach the maximum, a notification message is set in step 429 to be sent by telemetry to the clinician indicating that therapy delivery device 14 is unable to reduce neural activity to the desired level.

Figure 35:
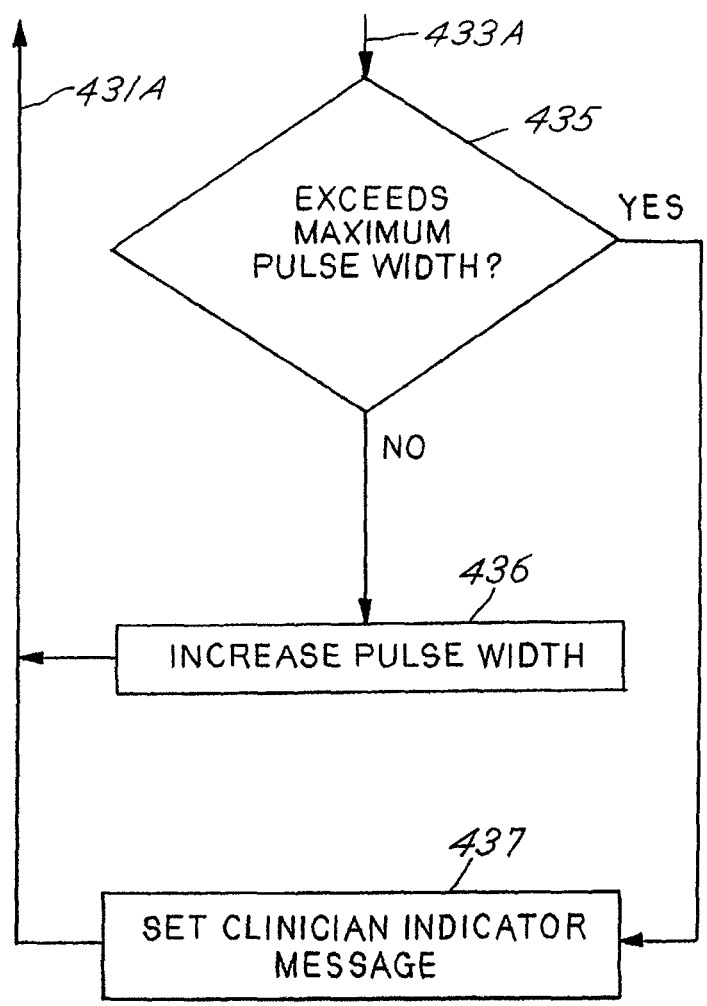

If, on the other hand, the stimulation electrode is placed in a location which the clinician would like to activate to alter the symptoms of the neurological disorder, the algorithm would follow a different sequence of events. In the preferred embodiment, the frequency parameter would be fixed at a value chosen by the clinician to facilitate neuronal activity in step 430 (FIG. 34) through path 420A (FIG. 32). In steps 431 and 432 the algorithm uses the values of the feedback sensor to determine if neuronal activity is being adequately controlled. In this case, inadequate control indicates that the neuronal activity of the stimulation target is too low. Neuronal activity is increased by first increasing stimulation amplitude (step 434) provided it doesn't exceed the programmed maximum value checked for in step 433. When maximum amplitude is reached, the algorithm increases pulse width to its maximum value in steps 435 and 436 (FIG. 35). A lack of adequate alteration of the symptoms of the neurological disorder, even though maximum parameters are used, is indicated to the clinician in step 437. After steps 434, 436 and 437, the algorithm returns to step 431 through path 431A, and the feedback sensor again is read.

It is desirable to reduce parameter values to the minimum level needed to establish the appropriate level of neuronal activity in the spinal cord. Superimposed on the algorithm just described is an additional algorithm to readjust all the parameter levels downward as far as possible. In FIG. 31, steps 410 through 415 constitute the method to do this. When parameters are changed, a timer is reset in step 415. If there is no need to change any stimulus parameters before the timer has counted out, then it may be possible due to changes in neuronal activity to reduce the parameter values and still maintain appropriate levels of neuronal activity in the target neurons. At the end of the programmed time interval, signal generator 14 tries reducing a parameter in step 413 to determine if control is maintained. If it is, the various parameter values will be ratcheted down until such time as the sensor values again indicate a need to increase them. While the algorithms in FIGS. 31-35 follow the order of parameter selection indicated, other sequences may be programmed by the clinician.

The stimulation might be applied periodically during the period of stimulation/infusion either routinely or in response to sensor or patient generated demand. Alternatively, in the case of simultaneous stimulation and drug therapy, stimulation could be applied continuously with infusion occurring periodically. Patient activation of either infusion or stimulation may occur as a result of an increase in symptoms being experienced by the patient. Alternatively, the infusion of an agent to activate a neuronal population might be alternated with application of electrical stimulation of that same population.

Advantageously, the present invention may be used to selectively position stimulation electrodes optimally closer to the targeted neural tissue to more effectively deliver a desired treatment therapy. Those skilled in that art will recognize that the preferred embodiments may be altered or amended without departing from the true spirit and scope of the invention, as defined in the accompanying claims. For example, the present invention may also be implemented within a drug delivery system and/or may be implemented to provide treatment therapy to other parts of the body such as the brain, nerves, muscle tissue, or neural ganglia. Further, the various embodiments of the present invention may be implemented within a percutaneous lead or a paddle lead.

The invention claimed is:

1. A medical device for providing therapy to a body comprising:
    a lead having a body with a plurality of therapy delivery elements; and
    a plurality of threaded collars adapted to be screwed into bone of a patient, each threaded collar defining a proximal opening in a top portion of the threaded collar, a passageway through the threaded collar, and a distal opening, wherein each of the threaded collars is coupled to the body of the lead such that the body of the lead is disposed distally of the distal opening of each threaded collar.

2. The medical device according to claim 1, wherein at least one therapy delivery element is an electrode.

3. The medical device according to claim 1, further comprising a means for positioning at least one therapy delivery element closer to a target site of a patient.

4. The medical device according to claim 1, wherein at least one threaded collar comprises a threaded inner housing, wherein at least one threaded inner housing defines the distal opening, the passageway, and the proximal opening.

5. The medical device according to claim 4, wherein the top portion of at least one threaded inner housing comprises a cavity adapted to be turned by a screwdriver-like device.

6. The medical device according to claim 4, wherein the top portion of at least one threaded inner housing comprises a cavity adapted to be turned by a slotted screwdriver-like device.

7. The medical device according to claim 4, wherein the top portion of at least one threaded inner housing comprises a hexagonal cavity adapted to be turned by a hexagonal wrench-like device.

8. The medical device according to claim 4, wherein the top portion of at least one threaded inner housing comprises a hexagonal cavity adapted to be turned by a percutaneous needle.

9. The medical device according to claim 4, further comprising a means for positioning at least one therapy delivery element closer to a target site of a patient.

10. The medical device according to claim 4, further comprising a swivel mechanism to allow turning of the threaded inner housing but not the corresponding body of the lead.

11. The medical device according to claim 4, further comprising a ball and socket to allow turning of the threaded inner housing but not the corresponding body of the lead.

12. The medical device according to claim 4, wherein at least one therapy delivery element is an electrode.

13. The medical device according to claim 4, wherein the body of the lead is coupled to the threaded inner housing such that movement of the threaded inner housing within the collar moves the body of the lead.

* * * * *